(12) United States Patent
Raz et al.

(10) Patent No.: US 12,148,229 B2
(45) Date of Patent: Nov. 19, 2024

(54) SYSTEM, DEVICE, AND METHOD FOR VEHICLE POST-CRASH SUPPORT

(71) Applicant: GUARDIAN OPTICAL TECHNOLOGIES LTD, Tel Aviv (IL)

(72) Inventors: Guy Raz, Binyamina (IL); Tal Recanati, Tel Aviv (IL)

(73) Assignee: GENTEX CORPORATION, Zeeland, MI (US)

( * ) Notice: Subject to any disclaimer, the term of this patent is extended or adjusted under 35 U.S.C. 154(b) by 362 days.

(21) Appl. No.: 17/419,213

(22) PCT Filed: Dec. 28, 2019

(86) PCT No.: PCT/IL2019/051422
§ 371 (c)(1),
(2) Date: Jun. 28, 2021

(87) PCT Pub. No.: WO2020/136658
PCT Pub. Date: Jul. 2, 2020

(65) Prior Publication Data
US 2022/0067410 A1  Mar. 3, 2022

Related U.S. Application Data

(60) Provisional application No. 62/785,724, filed on Dec. 28, 2018.

(51) Int. Cl.
*G06V 20/59* (2022.01)
*A61B 5/00* (2006.01)
(Continued)

(52) U.S. Cl.
CPC ............ *G06V 20/59* (2022.01); *A61B 5/0205* (2013.01); *A61B 5/6893* (2013.01); *G06T 7/73* (2017.01);
(Continued)

(58) Field of Classification Search
CPC ...... G06V 20/59; G06V 40/15; A61B 5/0205; A61B 5/6893; A61B 5/02416;
(Continued)

(56) References Cited

U.S. PATENT DOCUMENTS 8,823,552 B1 * 9/2014 Raphael ................ B60Q 1/247
340/932.2
9,886,841 B1   2/2018 Nave et al.
(Continued)

FOREIGN PATENT DOCUMENTS

KR    20180120901 A   11/2018
WO   WO 2017158155 A1   9/2017
WO      2018146266 A1    8/2018

OTHER PUBLICATIONS

Yuan et al. (2018). Hetero-ConvLSTM: A Deep Learning Approach to Traffic Accident Prediction on Heterogeneous Spatio-Temporal Data. In KDD '18: Proceedings of the 24th ACM SIGKDD International Conference on Knowledge Discovery & Data Mining, Jul. 2018 pp. 984-992. Retrieved Jul. 13, 2021 from: https://dl.acm.org/doi/pdf/10.1145/3219819.3219922.
(Continued)

*Primary Examiner* — Farzana Hossain
(74) *Attorney, Agent, or Firm* — Price Heneveld LLP; Brian James Brewer

(57) ABSTRACT

System and methods are provided for providing first responders after a vehicle accident with useful information regarding the medical status and injuries of the vehicle's occupants. The system includes an in-cabin sensor comprising at least one or more of an image sensor, depth sensor and micro-vibration sensor for capturing sensory data of the vehicle cabin including pre-crash data, during-crash and post-crash. The system also includes at least one processor configured to analyze the sensory data.

16 Claims, 21 Drawing Sheets

(51) Int. Cl.
    *A61B 5/0205*     (2006.01)
    *A61B 5/024*     (2006.01)
    *A61B 5/08*     (2006.01)
    *G06T 7/73*     (2017.01)
    *G16H 40/63*     (2018.01)
    *H04N 13/254*     (2018.01)

(52) U.S. Cl.
    CPC ........... G16H 40/63 (2018.01); H04N 13/254 (2018.05); *A61B 5/02416* (2013.01); *A61B 5/0816* (2013.01); *G06T 2207/10028* (2013.01); *G06T 2207/30196* (2013.01); *G06T 2207/30268* (2013.01)

(58) Field of Classification Search
    CPC . A61B 5/0816; A61B 5/7264; A61B 2505/01; A61B 2576/00; A61B 5/0077; A61B 5/024; G06T 7/73; G06T 2207/10028; G06T 2207/30196; G06T 2207/30268; G16H 40/63; G16H 30/40; G16H 50/20; H04N 13/254; G07C 5/008; G08B 25/00
    See application file for complete search history.

(56) References Cited

U.S. PATENT DOCUMENTS

| | | |
|---|---|---|
| 2003/0015898 A1 | 1/2003 | Breed |
| 2003/0122554 A1 | 7/2003 | Karray et al. |
| 2004/0220705 A1 | 11/2004 | Basir et al. |
| 2005/0201103 A1 | 9/2005 | Saccomanno et al. |
| 2008/0146952 A1* | 6/2008 | Presura .............. A61B 5/02444 600/508 |
| 2008/0212836 A1 | 9/2008 | Fujimura et al. |
| 2008/0243332 A1 | 10/2008 | Basir et al. |
| 2009/0066065 A1 | 3/2009 | Breed et al. |
| 2009/0096783 A1 | 4/2009 | Shpunt et al. |
| 2012/0078472 A1 | 3/2012 | Neal et al. |
| 2014/0300739 A1 | 10/2014 | Mimar |
| 2015/0313475 A1 | 5/2015 | Benson et al. |
| 2015/0379362 A1 | 12/2015 | Calmes et al. |
| 2018/0086264 A1 | 3/2018 | Pedersen |
| 2019/0092258 A1* | 3/2019 | Salter ................. B60R 21/0132 |
| 2019/0357834 A1* | 11/2019 | Aarts ................. A61B 5/7246 |
| 2020/0293750 A1* | 9/2020 | Zuta ...................... G06V 20/10 |
| 2022/0270180 A1* | 8/2022 | Leise ..................... G06N 20/00 |
| 2022/0292705 A1* | 9/2022 | Friedman .............. G06V 10/82 |

OTHER PUBLICATIONS

PCT International Search Report for International Application No. PCT/IL2019/51422, mailed Apr. 27, 2020, 3pp.
PCT Written Opinion for International Application No. PCT/IL2019/51422, mailed Apr. 27, 2020, 18pp.

\* cited by examiner

SYSTEM, DEVICE, AND METHOD FOR VEHICLE POST-CRASH SUPPORT

CROSS-REFERENCE

The present application is a National Phase of PCT Patent Application No. PCT/IL2019/051422 having International filing date of Dec. 28, 2019, which claims priority to U.S. Provisional Application Ser. No. 62/785,724 filed on Dec. 28, 2018, entitled "SYSTEM, DEVICE AND METHOD FOR VEHICLE POST-CRASH SUPPORT", the contents of which are all incorporated herein by reference in their entirety.

TECHNICAL FIELD

The present invention, in some embodiments thereof, relates to a system and method for analyzing in-cabin data to provide medical related information following a vehicle accident.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BACKGROUND OF THE INVENTION

When a vehicle accident, such as a car accident occurs, the correct action of first responders and medical teams can have long term significance. Understanding the nature and the severity of the injury of the car occupants can improve the response in terms of prioritizing and immediate treatment. It can also help to direct the right first responders' teams thereby shortening the time required for the right equipment to arrive at the scene.

While there is a large effort to reduce the number and severity of vehicle accidents, vehicle accidents do keep occurring and unfortunately will do so for the foreseeable future.

Currently, there is no way for the rescue team to know in advance what is the situation inside the vehicle, and typically updates regarding the medical condition of the occupants are received only when arriving at the scene. Moreover, even when the rescue team arrives at the scene, the only available information is obtained by visual inspection and by communicating with the involved occupants, if such communication is possible. Such communication, while providing important information, is limited by the level of consciousness and knowledge of the occupants.

In light of the above, there still remains an unmet need for an in-cabin system that can provide, for example in real-time, medically relevant information as to the post-crash status of the occupant. Such a system would improve the prospects of surviving a vehicle accident as well as reduce the long-term medical implications. It would also lead to economic benefit which might have an impact on insurance cost.

SUMMARY OF THE INVENTION

The present disclosure provides a system, device and method to evaluate the medical condition of one or more vehicle-occupants, for example in post-crash situation.

According to one embodiment, there is provided a system for detecting breathing or heartbeat of a vehicle occupant. The system comprises at least one illumination source configured to project light in a predefined light pattern on a scene; an imaging device configured to capture a plurality of images, said plurality of images comprising reflections of said light pattern from one or more occupants in the scene; and at least one processor configured to extract breathing or heartbeat data of said one or more occupants by analyzing the reflections of said light pattern.

The present disclosure also provides a method for analyzing heartbeat or breathing signals from said plurality of images of the said reflected light pattern. According to an embodiment, the analysis comprises the following steps: detecting one or more changes in one or more speckle patterns of at least one of the reflections of said light pattern in at least some consecutive images of the plurality of images; identifying micro-vibrations of the at least one object based on said speckle pattern analysis; and analyzing said micro-vibrations to extract breathing or heartbeat signal. In some embodiments, the breathing or heartbeat signal is used to assess the medical condition of the occupant. In some embodiments, the system comprises the use of an illumination source in the near infra-red (NIR) spectral range.

In an embodiment, the system comprises a communication module configured to send the medical-related data to a first responder's rescue team.

In an embodiment, the data is uploaded to a cloud service to be extracted by a first responders' rescue team.

In an embodiment, the system comprises a memory. In further embodiments, the system is configured to record post-crash images captured by the imaging device.

In an embodiment, said post-crash images are sent to a first responders' team by communication module or uploaded to a cloud service.

In an embodiment, the system is configured to store pre-crash images. In additional embodiments, the system is further configured to send the pre-crash images to a first responders' team or to upload said images to a cloud service to be extracted by a first responders' team.

In an embodiment, the processor is configured to analyze one or more post-crash images and extract a post-crash body pose thereby providing an assessment of the nature or severity of an injury.

In an embodiment, the processor is configured to analyze one or more stored pre-crash images in order to extract a pre-crash body pose. In further embodiments, the processor is configured to analyze said pre-crash body pose, optionally in combination with any available information regarding the physical parameters of the impact, thereby providing an assessment of the nature or severity of an injury.

In an embodiment, the processor is configured to analyze one or more pre-crash images in order to extract at least one body attribute including, but not limited to, mass, height, width, volume, age, and gender. In some embodiments, the processor is further configured to use said at least one body attribute, optionally in combination with any available information regarding the physical parameters of the impact, in order to analyze and assess the nature or severity of an injury.

In an embodiment, the assessment is sent to a first responders' team by communication module or uploaded to a cloud service.

In an embodiment, the system is triggered to initiate the analysis of the nature or severity of injury by utilizing vehicle impact sensors. In various embodiments, a vehicle impact sensor comprises a microswitch located inside the vehicle's bumper, said microswitch is configured to detect strong impacts. In an embodiment, the system uses the same sensors as the vehicle's airbag deployment system.

In an embodiment, the system is triggered to initiate the analysis by visually detecting rapid hectic motion of an occupant inside the vehicle. An example for such a detection mechanism is based on optical flow algorithm configured to analyze the relative displacement of objects between two or more consecutive frames.

According to an embodiment, the system comprises at least one high speed imaging device. In certain embodiments, the high speed imaging device is configured to capture a plurality of images at high rate during accident occurrence. In further embodiments, the system processor is configured to analyze said high rate images thereby assessing the nature or severity of injuries. In additional embodiments, the assessment is based on visually tracking the impacts occurring inside the cabin during the accident.

According to an embodiment, the system comprises a depth sensor configured to produce an in-cabin depth map.

In an embodiment, the system is configured to store the depth data.

In an embodiment, the processor is configured to use the depth map to analyze post-crash body pose thereby assessing the nature and severity of an injury.

In an embodiment, the processor is configured to analyze the stored pre-crash depth map thereby providing information regarding a pre-crash body pose of a vehicle occupant. In several embodiments, the processor is further configured to use said body pose, optionally in combination with any available information regarding the physical parameters of the impact, in order to analyze and assess the nature or severity of an injury.

In an embodiment, the processor is configured to analyze one or more pre-crash depth maps to extract a body attribute including, but not limited to, mass, height, width, volume, age, and gender. In further embodiments, the processor is further configured to use the at least one body attribute, optionally in combination with any available information regarding the physical parameters of the impact, in order to analyze and assess the nature or severity of an injury.

In an embodiment, the analysis comprises the use of a combination of at least one image and at least one depth map.

In an embodiment, the system uses a deep learning method such as, but not limited to, convolutional neural network, in order to provide said analysis.

According to another aspect there is provided a system for providing medical information of at least one occupant in a vehicle cabin, the system comprising: a sensing module comprising at least one sensor configured to capture sensory data of the vehicle cabin; and a control module comprising at least one processor said processor is configured to: receive said sensory data from said sensor; and analyze said sensory data using one or more analysis methods to provide the medical information of said at least one occupant.

In an embodiment, the analysis methods are one or more of: computer vision methods; machine learning methods; deep neural network methods; signal processing methods.

In an embodiment, the medical information comprises the medical status of said at least one vehicle occupant following an accident of said vehicle.

In an embodiment, the medical information comprises medical condition evaluation or injury assessment of the at least one occupant.

In an embodiment, the information comprises the medical status of said at least one vehicle occupant following an accident of the vehicle.

In an embodiment, the system comprises a communication module configured to send the information to a first responder team.

In an embodiment, the at least one sensor is an image sensor.

In an embodiment, the sensing module further comprises at least one illuminator, said at least one illuminator comprises a light source configured to project light pattern onto the vehicle cabin.

In an embodiment, the light source comprises a laser or a Light Emitting Diode (LED).

In an embodiment, the light source comprises one or more optical elements for splitting a single light beam generated by the light source, said one or more optical elements are selected from the group consisting of: DOE; split mirrors; and diffuser.

In an embodiment, the sensing module comprises a depth sensor.

In an embodiment, the depth sensor is configured to capture depth data by projecting a light pattern onto the vehicle cabin and wherein the at least one processor is configured to analyze the location of known light pattern elements in said depth data.

In an embodiment, the pose of said at least one occupant is estimated by analyzing the depth data using said computer vision methods.

In an embodiment, the sensing module comprises a micro-vibration sensor.

In an embodiment, the micro-vibration sensor is configured to: project light onto the vehicle cabin scene; capture a plurality of images, wherein each image of said plurality of images comprises reflected diffused light elements; and wherein the processor is configured to: receive the captured images; and analyze one or more temporal changes in the speckle pattern of at least one of the plurality of reflected diffused light elements in at least some consecutive images of the plurality of images to yield micro-vibration data.

In an embodiment, the sensing module comprising a combination of at least two sensors selected from a comprising: image sensor, depth sensor, and micro-vibration sensor.

In an embodiment, the processor is further configured to classify or identify an attribute of one or more objects based on at least one micro-vibration data.

In an embodiment, the sensory data comprises a plurality of images and wherein the at least one processor is further configured to classify the at least one vehicle occupant using said computer vision methods by visually analyzing at least one image of the plurality of images captured by the at least one sensor.

In an embodiment, the sensing module is configured to detect an imminent crash of the vehicle.

In an embodiment, the detection of an imminent crash is performed by one or more of: vehicle impact sensor; hectic movement detection sensor; and external sensory system.

In an embodiment, the at least one processor is configured to: analyze said sensory data, wherein said sensory data is captured prior to said detection of imminent crash, during said crash and following said crash; and asses the medical status of said at least one vehicle occupant following the crash based on said analyzed sensory data.

In an embodiment, the sensory data captured prior to the detection of the imminent crash is analyzed using said machine vision methods to extract pre-crash categorization.

In an embodiment, the pre-crash categorization comprises one or more of the at least one occupant body pose, body mass, age, body dimensions, and gender.

In an embodiment, the system is configured to provide a measure of the likelihood and severity of an injury from a car accident In an embodiment, the system is configured to provide high-rate data of the vehicle cabin following the detection of the imminent crash.

In an embodiment, the high-rate data is used to extract trajectories of the at least one occupant or one or more objects in the vehicle.

In an embodiment, the extracted trajectories are used to asses the likelihood and severity of the injury of said at least one occupant.

In an embodiment, the system is configured to record in-cabin post-crash information; and assess the medical status of at least one car occupant.

In an embodiment, the system is configured to provide at least one of pre-crash, during-crash and post-crash medical status assessment of at least one car occupant.

In an embodiment, the control module is configured to be in wireless communication with an external and transmit the information to a first responder team.

In an embodiment, the information is uploaded to a cloud service.

In an embodiment, the sensing module is mounted on said vehicle roof or ceiling.

In an embodiment, the analysis is conducted using at least one deep learning algorithm.

According to another aspect there is provided a system for estimating the medical state of one or more occupants in a vehicle cabin following an accident of the vehicle, the system comprising; a sensing module comprising: an illuminator comprising one or more illumination sources configured to project light in a structured light pattern on the vehicle cabin; at least one image sensor configured to capture sensory data prior to, during and following a crash of said vehicle, said sensory data comprising a sequence of 2D (two dimensional) images and 3D (three dimensional) images of the vehicle cabin wherein at least one of the 2D images comprise reflections of said structured light pattern from the one or more occupants in the cabin; a control module comprising: a memory module; at least one processor, said at least one processor is configured to: receive said captured sensory data from the sensing module; receive an impact detection signal of an imminent crash of the vehicle; store the received sensory data, captured prior to said impact detection receptance, in said memory module; analyze said received sensory data using computer vision or machine learning algorithm to yield pre-crash assessment data comprising an identification of the one or more occupants state prior to the crash; receive sensory data captured during said crash from the sensing module; analyze the received sensory data captured during said crash to yield during-crash assessment data comprising body trajectories of the one or more occupants; provide medical information of said one or more occupants following the crash based on said during crash assessment data and pre-crash assessment data.

In an embodiment, the at least one processor is further configured to: receive sensory data captured following the crash; analyze the received sensory data captured following the crash data using computer vision or machine learning algorithm to yield one or more of post-crash assessment data of said one or more occupants.

In an embodiment, the post-crash assessment data comprises one or more of: heartbeat; respiration rate; body pose; body motion; visible wounds.

In an embodiment, the processor is further configured to combine said post-crash assessment data with said during crash assessment data and said pre-crash assessment data to yield said medical information of said one or more occupants following the crash.

In an embodiment, the heartbeat or respiration rate are identified by analyzing one or more changes in one or more speckle patterns of at least one of the reflections of said structured light pattern in at least some consecutive images of the plurality of images; and identify the vibrations of the one or more occupants based on said speckle pattern analysis.

In an embodiment, the one or more of the body pose, body motion; and visible wounds are detected by analyzing the sequence of 2D images or 3D images of the vehicle cabin In an embodiment, the body pose or body motion are identified using one or more of a skeleton model, optical flow of visual tracking methods.

According to another aspect, there is provided a method for providing medical information of at least one occupant in a vehicle cabin, the method comprising: receiving captured sensory data of said vehicle cabin from a sensing module; receiving an impact detection signal of an imminent crash of the vehicle; storing the received sensory data, captured prior to said impact detection receptance, in a memory module; analyzing said received sensory data using computer vision or machine learning algorithm to yield pre-crash assessment data comprising identification of the at least one occupant state prior to the crash; receiving sensory data captured during said crash from the sensing module; analyzing the received sensory data captured during said crash to yield during-crash assessment data comprising body trajectories of the one or more occupants; providing medical information of said one or more occupants following the crash based on said during crash assessment data and pre-crash assessment data.

According to another aspect, there is provided a method for providing a first responder with information regarding the medical status or injury of vehicle a vehicle occupant after an accident, the method comprises the steps of: i. utilizing an in-cabin sensor to monitor the vehicle's cabin;
ii. combining analysis of at least one of pre-crash, during-crash and post-crash data; and iii. providing first-responders with the analysis.

BRIEF DESCRIPTION OF THE DRAWINGS

A better understanding of the features and advantages of the present disclosure will be obtained by reference to the following detailed description that sets forth illustrative embodiments, in which the principles of embodiments of the present disclosure are utilized, and the accompanying drawings.

DETAILED DESCRIPTION OF THE INVENTION

Figure 1A:
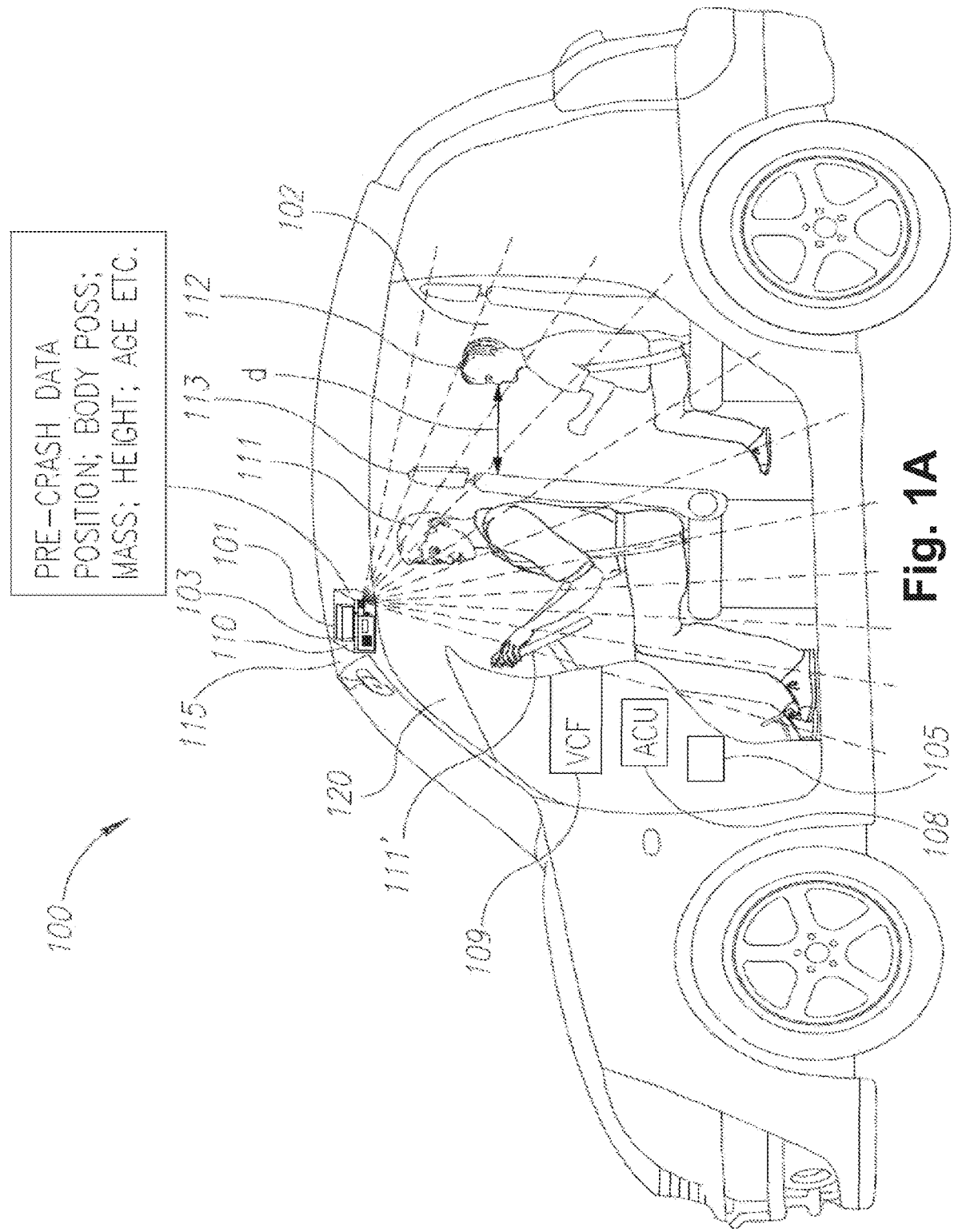
FIGS. 1A-1C illustrate, respectively, a side view of a vehicle prior to the vehicle's accident during the accident and following the accident, in accordance with some embodiments of the present disclosure.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore, the invention is not limited by that which is illustrated in the figure and described in the specification, but only as indicated in the accompanying claims, with the proper scope determined only by the broadest interpretation of said claims.

It is stressed that the particulars shown hereinabove are by way of example and for purposes of illustrative discussion of the preferred embodiments of the present invention only and are presented in the cause of providing what is believed to be the most useful and readily understood description of the principles and conceptual aspects of the invention.

The configurations disclosed herein can be combined in one or more of many ways to provide a way to inform first responders or rescue team information such as medical information including the status of the injured occupant(s), for example in a post-crash accident situation. One or more components and methods of the configurations disclosed herein can be combined with each other in many ways.

System and methods as described herein uses an in-cabin sensing module to monitor the medical status of a vehicle occupant as well as analyze possible injuries and their severity.

According to some embodiments, the system may be installed, and/or mounted, and/or integrated and/or embedded in a vehicle, specifically in a cabin of the vehicle.

According to some embodiments, the system comprises one or more imaging devices and optionally or additionally one or more illumination sources configured and enabled to project light in a predefined pattern on the in-cabin scene. The one or more imaging devices are configured to capture a plurality of images of the scene. The plurality of images can contain reflections of the light pattern from one or more objects in the scene (e.g. vehicle occupants). The system may also comprise one or more processors configured and enabled to analyze the plurality of captured images to conduct post-crash medical status analysis, and/or to monitor the medical condition of the vehicle occupants and/or analyze possible injuries of the occupants and their severity as detailed hereinbelow.

Alternatively or in combination, the one or more processors are configured to analyze a speckle content of the light pattern induced on the scene by the one or more illumination sources. The speckle pattern may be used to obtain the micro-vibrations pattern of the one or more objects in the scene.

According to one embodiment, when the one or more occupants are humans present at the scene, the micro-vibration signal may be correlated with breathing motion or with heartbeat induced skin motion or a combination thereof. The disclosed system can, therefore, monitor vital signs of the vehicle's occupants, for example in a post-crash situation.

Advantageously, the system provides both the vital signs signal of breathing or heartbeats and a plurality of image data of the post-crash cabin, all using a single device or system.

Moreover, the system provides both post-crash data, and pre-crash data that can be used to further assess the details and of an injury.

As used herein, like characters refer to like elements.

As used herein, the term "light" encompasses electromagnetic radiation having wavelengths in one or more of the ultraviolet, visible, or infrared (IR) portions, including shortwave IR, near IR, and long IR, of the electromagnetic spectrum.

The term "light pattern" as used herein is defined as the process of projecting a known pattern of pixels onto a scene. The term "pattern" is used to denote the forms and shapes produced by any non-uniform illumination, in particularly patterned illumination employed a plurality of pattern features, such as lines, stripes, dots, geometric shapes, etc., having a uniform or different characteristics such as shape, size, intensity etc. As a non-limiting example, a pattern light illumination pattern may comprise multiple parallel lines as pattern features.

The term "depth map" as used herein is defined as an image that contains information relating to the distance of the surfaces of a scene object from a viewpoint. A depth map may be in the form of a mesh connecting all dots with z-axis data.

The term "occupant" as used herein is defined as any individual present in a vehicle, including, the driver and any of the passengers. The term also includes non-human occupants.

The term "vehicle" as used herein refers to a private car, a commercial car, a truck, a bus, a transporter, drivable mechanical equipment or any compartment used to transport humans on roads or tracks.

The term "normal vehicle operation mode" as used herein refers to any operation of a vehicle for example on driving or while the vehicle stops prior to an accident of the vehicle.

The term "pre-crash data" as used herein refers to any type of data such as visual images, 3D images of objects within a vehicle obtained prior to the vehicle's crash.

The term "post-crash data" as used herein refers to any type of data such as visual images, 3D images of objects within a vehicle obtained following the vehicle's crash.

Figure 1B:
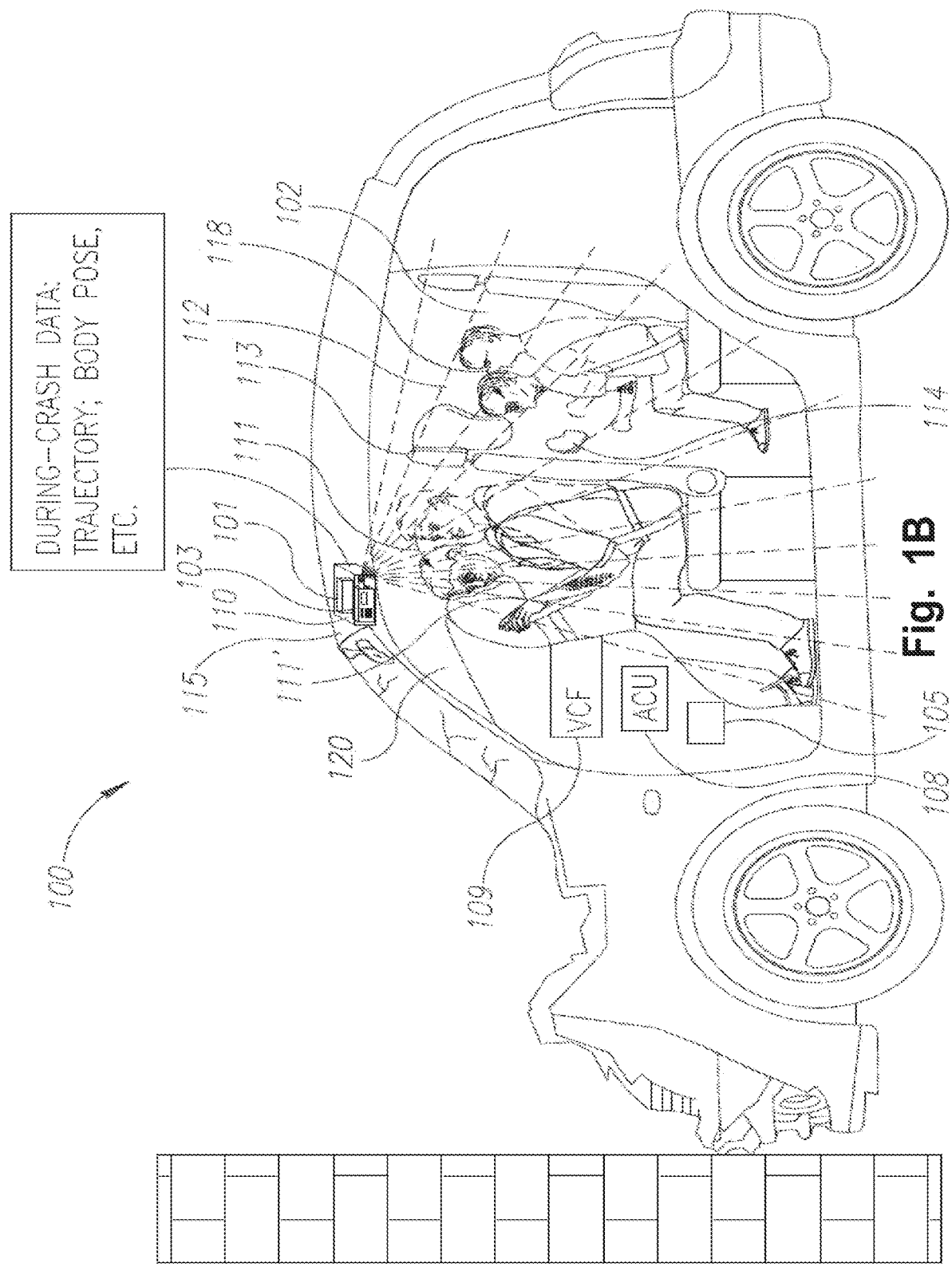
Figure 1C:
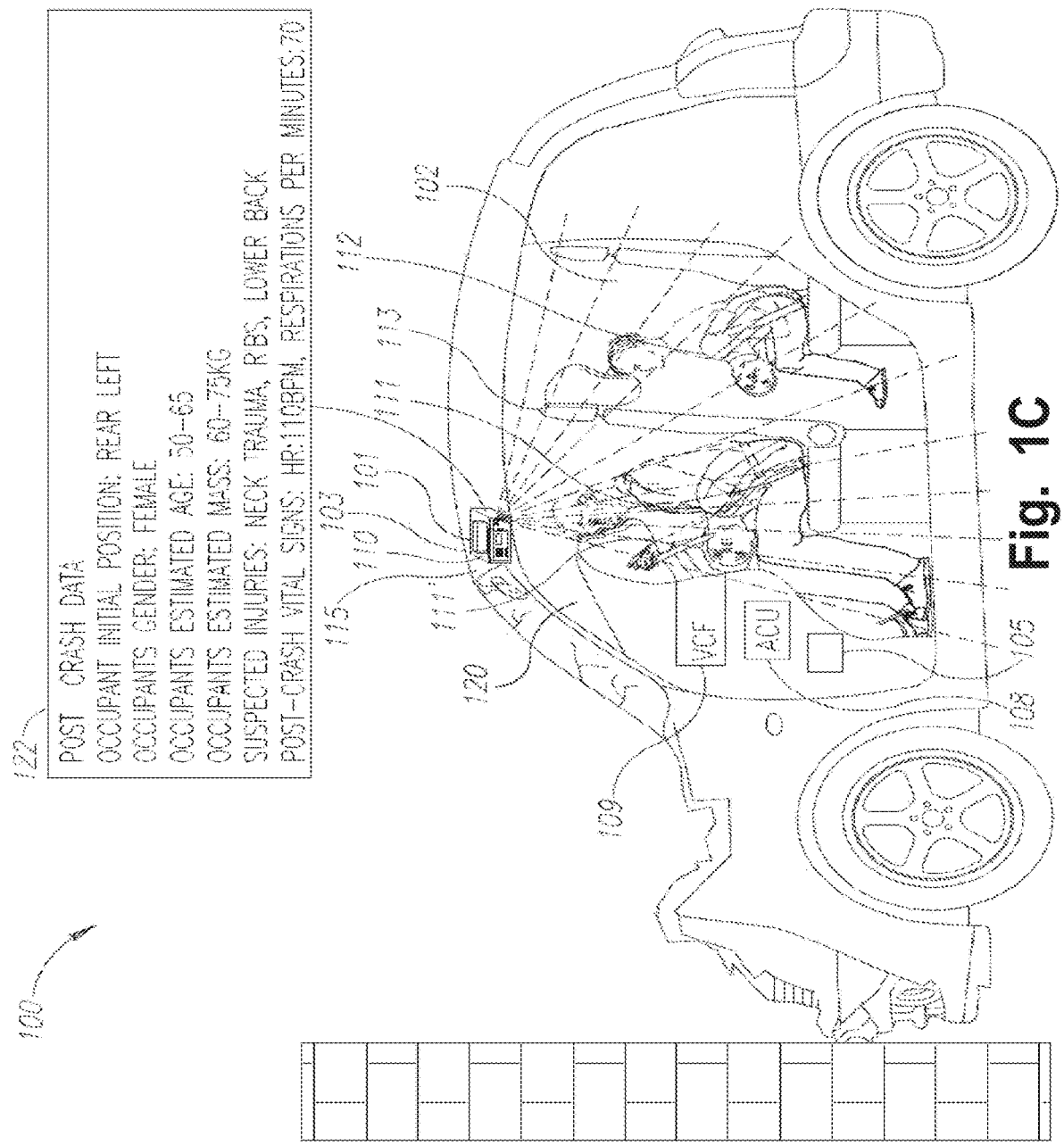

Referring now to the drawings, FIG. 1A, FIG. 1B and FIG. 1C illustrate, respectively a side view of a vehicle 100 and a passenger cabin 120 prior to the vehicle's accident (FIG. 1A) during the accident (FIG. 1B) and following the accident (FIG. 1C), in accordance with embodiments. The vehicle 100 includes a sensing system 110, configured and enabled to capture and obtain data before the accident (e.g. pre-crash data), during the accident (e.g. during-crash data) and after the accident occurs (post-crash data). Each data may include visual (e.g. video images) and stereoscopic data (e.g. depth maps), for example, 2D (two dimensional) images and/or 3D (three dimensional) images and vibration data (e.g. micro-vibrations) of areas and objects within the vehicle 100. Each data may be analyzed, for example in real-time or close to real-time, to assess the medical status of one or more occupants following the vehicle accident, in accordance with embodiments.

Specifically, the sensing system 110 is configured to monitor areas and objects within the vehicle before an accident occurs, during the accident and following the accident to obtain various types of sensory data of the areas and objects (e.g. occupants), and analyze the obtained data, using one or more processors, to extract visual data and depth data and to detect speckle pattern dynamic for identifying vibrations (e.g. micro-vibrations) and use the extracted data to estimate the medical status of the occupants. Nonlimiting examples of such objects may be one or more of the vehicle's occupants such as driver 111 or passenger(s) 112, in accordance with embodiments.

More specifically, there are provided methods and systems configured to analyze the captured sensory data to detect the occupants pose and location before an accident occurs, as well as their trajectory 118 resulted from the vehicle crash and finally the accident results (e.g. post-crash data) including medical information such as information related to the occupants wounds and heartbeat. In some cases, the medical information may be transmitted to external units and forces such a rescue team, for example in real-time, in accordance with embodiments.

According to some embodiments, the sensing system 110 may be connected or may be in communication with the vehicle's units such as the vehicle's sensors such as impact detection sensor or 105 and/or airbag control unit (ACU) 108 and/or to Vehicle Computing System (VCS) 109 and/or a collision avoidance system (CAS) 105. For example, the sensing system may receive one or more signals including additional sensory data from CAS 105. The sensing system 110 may be in communication with other types of sensors of the vehicle such as an accelerometer and may fuse and use the additional data with the extracted data to estimate the medical status of the occupants.

Specifically, according to some embodiments, the sensing system 110 may be connected to or may be in communication, such as wireless communication, with the vehicle's CAS which is configured to prevent or reduce the severity of a collision. An example of such CAS may include radar (all-weather) and/or laser (LIDAR) and camera (employing image recognition) to detect an imminent crash. The sensing system 110 may combine the data received from the CAS with the extracted data use data to estimate the medical status of the occupants, for example following the vehicle's collision.

According to some embodiments, the sensing system 110 may be mounted at the cabin's ceiling or roof, for example in the front section 115 of the vehicle's roof, in a way that allows a full cabin view. According to some embodiments, the sensing system 110 may be installed, mounted, integrated and/or embedded in a vehicle, specifically in a cabin of the vehicle such that the scene is the cabin interior 120 and the object(s) present in the cabin may include, for example, one or more of: vehicle occupant(s) (e.g. a driver(s), passenger(s), pet(s), etc.); one or more objects associated with the cabin (e.g. seat, door, window, headrest, armrest, etc.); items associated with one or more of the vehicle occupant(s) (e.g. an infant seat, a pet cage, a briefcase, a toy, etc.) and/or the like.

It is stressed that one of the main advantages of mounting the system 110 in the vehicle's roof or ceiling is that in this location in the vehicle the system 110 is less exposed to damages and to strong impacts during accidents.

According to some embodiments, the systems and methods are configured to generate an output, such as one or more output signals including medical information, such as medical status in real-time, of the one or more occupants following the vehicle's accident.

Figure 3A:
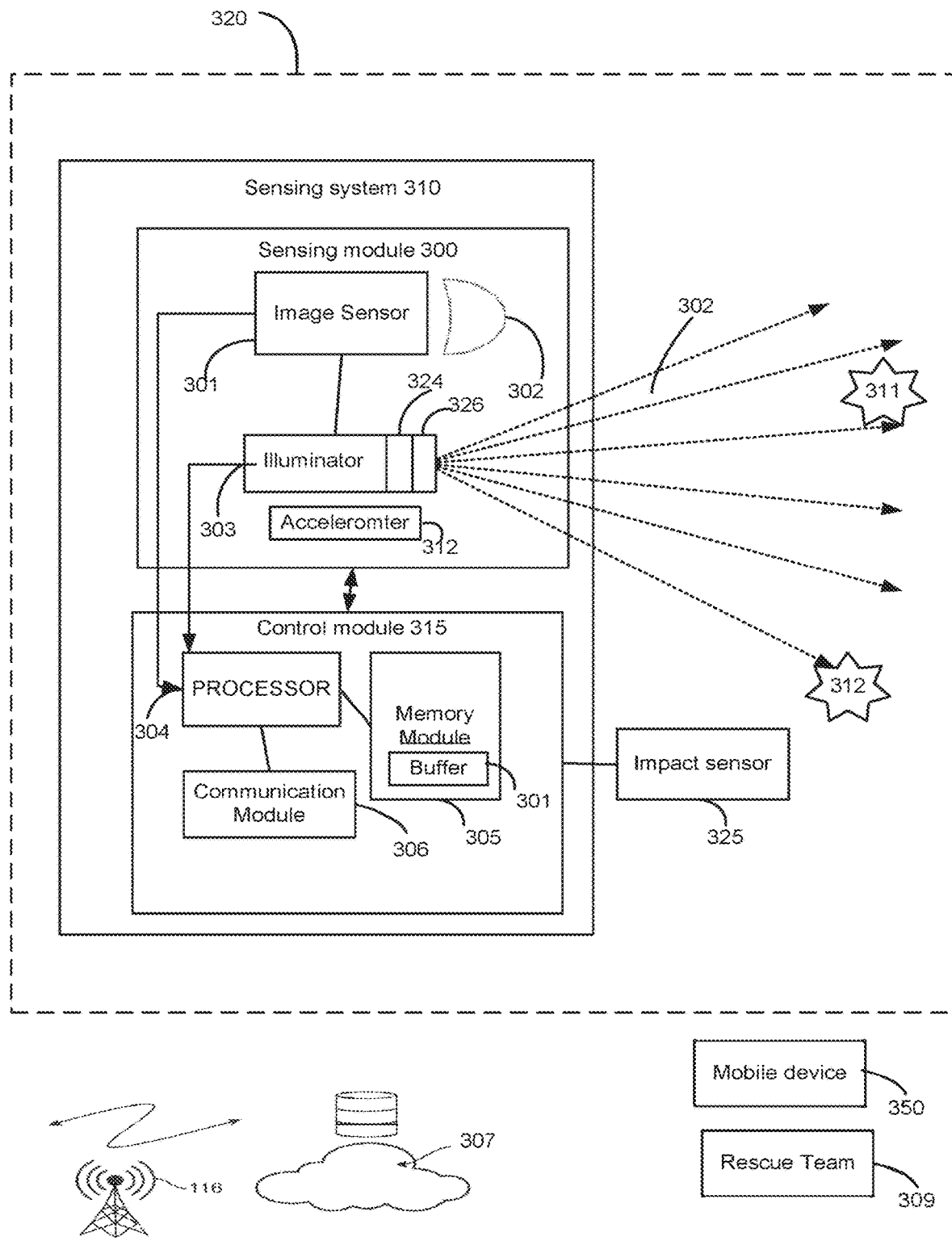
FIG. 3A shows a high-level block design of the system comprising a sensing module and a control module, in accordance with some embodiments of the present disclosure.
Figure 3B:
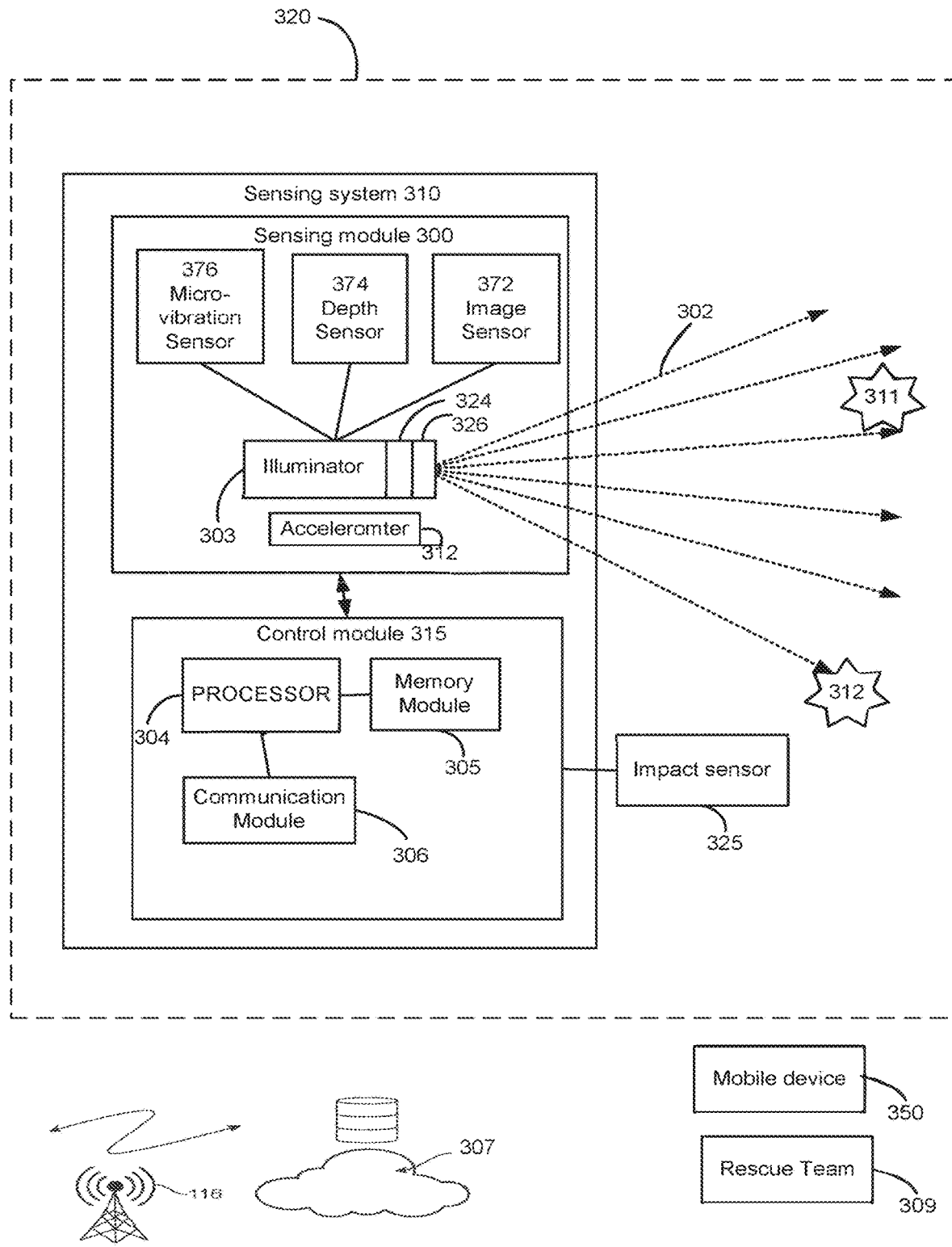
FIG. 3B shows a high-level block design of the system comprising different types of sensors, in accordance with some embodiments of the present disclosure.

According to some embodiments, the sensing system 110 may include one or more sensors, for example of different types, such as a 2D imaging sensor and/or a 3D imaging sensor (e.g. stereoscopic camera) and/or an RF imaging sensor and/or a vibration sensor (micro-vibration), structured light sensor, ultrasonic sensor and the like to capture sensory data of the vehicle cabin, as will be further illustrated in FIG. 3B. Specifically, the 2D imaging sensor may capture images of the vehicle cabin, for example from different angels, and generate original visual images of the cabin. In an embodiment, the sensing system 110 may include an imaging sensor configured to capture 2D and 3D images of the vehicle cabin and at least one processor to analyze the images to generate a depth map of the cabin.

In another embodiment, the system 110 may detect vibrations (e.g. micro-vibrations) of one or more objects in the cabin using one or more vibration sensors and/or analyzing the captured 2D or 3D images to identify vibrations (e.g. micro-vibrations) of the objects.

According to another embodiment, the system 110 may further include a face detector sensor and/or face detection and/or face recognition software module for analyzing the captured 2D and/or 3D images.

In an embodiment, the system 110 may include or may be in communication with a computing module comprising one or more processors configured to receive the sensory data captured by the system's 110 sensors and analyze the data according to one or more of computer vision and/or machine learning algorithms to yield medical information including an estimation the medical condition of the one or more occupants in the vehicle cabin as will be illustrated hereinbelow.

Specifically, in accordance with embodiments, the one or more processors are configured to combine various types of sensory data (e.g. 2D data (e.g. captured 2D images) 3D data (depth maps)) of the vehicle cabin along a period of time such few seconds or minutes (e.g. 1, 2, 3, 4-100 seconds and more) before an accident, during the accident and following the accident to yield the medical information relating to the one or more occupants in the vehicle cabin.

Advantageously, system 110 provides merely the minimal hardware such as one or more sensors and imagers for capturing visual and depth images of the vehicle 110 interior. In some cases, an interface connecting to system 110 may supply the necessary power and transfer the data acquired to the vehicle's computing and/or processing units such as VCS 109 and/or ACU 108, where all the processing is being carried out, taking advantage of its computing power. Thus, in accordance with some embodiments, installing system 110 becomes very easy and using off-the-shelf components.

Figure 2A:
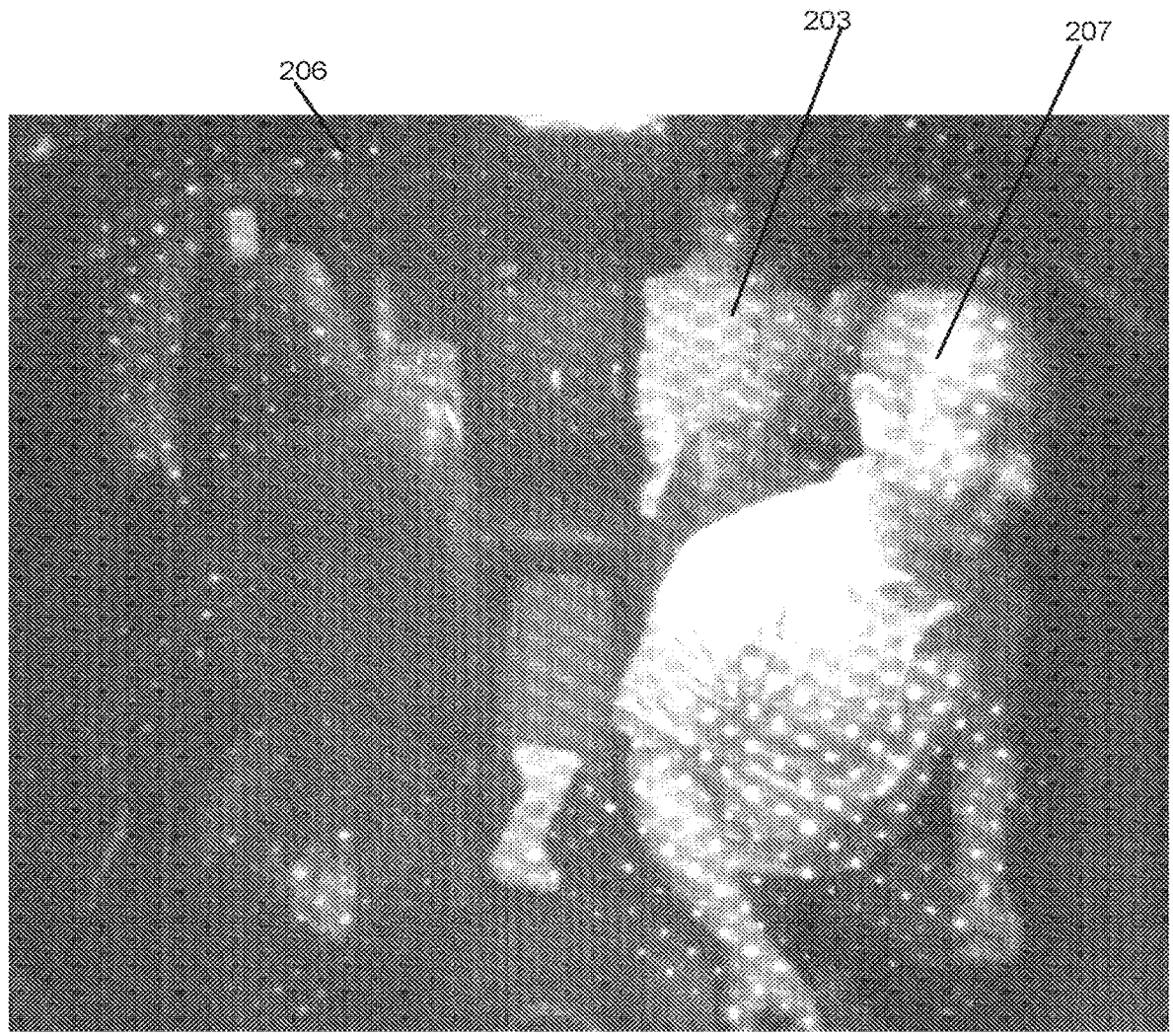
FIG. 2A shows an example of system raw data, in accordance with some embodiments of the present disclosure.

According to some embodiments, the sensing system 110 comprises one or more illuminators such as an illuminator 103 and a sensor 101. The illuminator 103 creates light such as a pattern of light, schematically indicated here as rays of spots 102. In some cases, the created light pattern may cover all or selected portions of the occupants of vehicle 100 such as passenger 203 and driver 207 as shown in FIG. 2A.

According to some embodiments, sensor 101 may be selected from a group consisting of: a Time of Flight (ToF) image sensor; a camera; RF (radio frequency) device; stereoscopic camera, structured light sensor, ultrasonic sensor.

According to some embodiments, the sensor 101 may be an image sensor equipped with a fish-eye lens allowing coverage of the full cabin. In some cases, to cover all possible positions of the occupants in a vehicle a typical coverage of more than 150 degrees may be used. The sensor may be a CMOS sensor (Complementary Metal Oxide Semiconductor) or CCD sensor (charge-coupled device) with resolution such as VGA, 2MP, 5MP, 8MP. The and lens can work in the visible range, or IR range.

According to some embodiments, the illuminator 103 creates a light pattern that may cover one or more portions or the whole cabin 120. An example of such a pattern is a spot pattern. FIG. 2A shows such an example of a spot pattern 206 covering the front and back seat in a standard passenger's car. The pattern can be spots pattern, as shown in FIG. 2A, lines, grid, or any other pre-configured shape. Advantageously, having the light concentrated in small regions such as the spot shown in FIG. 2A, may improve the signal to background ratio and hence provide a clearer speckle signal.

Figure 2B:
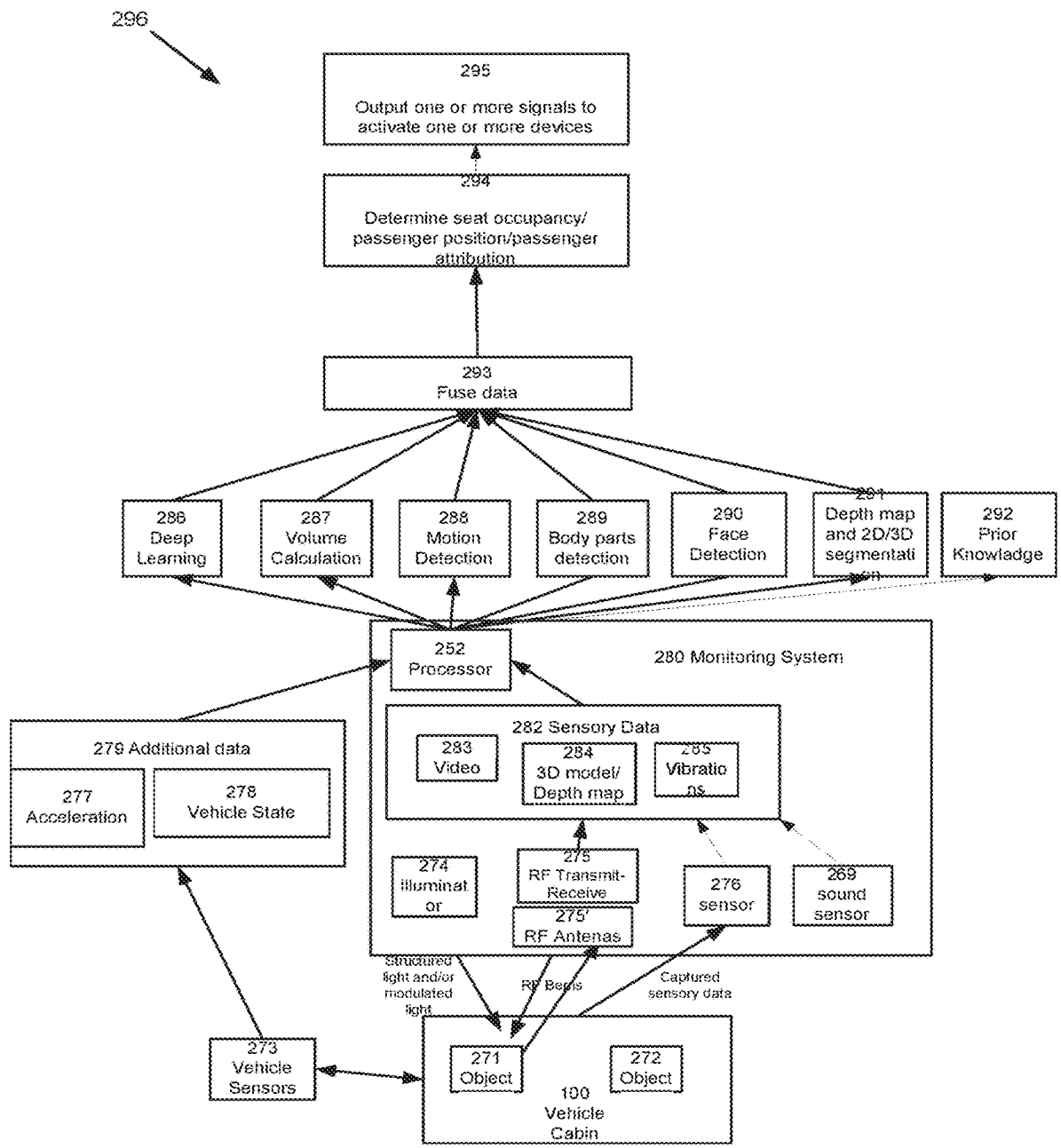
FIG. 2B is a flow diagram illustrating steps of identifying objects, such as hidden objects in a vehicle cabin and providing information on the identified objects, in accordance with some embodiments of the present disclosure.

FIG. 2B is a flow diagram 296 illustrating steps of detecting occupancy state, including identifying objects, such as hidden objects in a vehicle cabin and providing information on the identified objects, according to one embodiment. As shown in FIG. 2B, a sensing system 280 includes one or more illumination units such as an illuminator 274 which provides structured light with a specific illumination pattern (e.g., spots or strips or other patterns) to objects 271 and 272 located for example at the rear section in the vehicle cabin 100 and one or more sensors such as sensor 276 captures an image of the objects 271 and 272 in the vehicle cabin 100.

According to one embodiment, the sensing system 280 may include one or more processors such as processor 252. The processor 252 may be in wired or wireless communication with devices and other processors. For example, the output from processor 252 may trigger a process within the processor 252 or may be transmitted to another processor or device to activate a process at the other processor or device.

According to another embodiment, the processor 252 may be external to the sensing system 280 and may be embedded in the vehicle or may be part of the vehicle's processing unit.

In one embodiment, the processor 252 may instruct the illuminator 265 to illuminate specific areas in the vehicle cabin.

According to some embodiments, the sensing system 280 may further include an RF transmit-receive unit 275 including, for example, an RF transmit-receive unit 275 for such as an RF transceiver configured to generate and direct RF beams towards the objects 271 and 272 using RF antennas 275 and receive the reflected RF beams to provide an RF image of the vehicle cabin 100 and objects 271 and 272. The captured images, including for example the RF signals and reflected pattern images are provided to the processor 252 to generate a depth map representation 291 and 2D/3D segmentation of the vehicle cabin 100 and/or the objects 271 and 272.

According to one embodiment, the sensing system may include a sound sensor 269 such as one or more ultrasound sensors and/or a directional microphone configured and enabled to detect the presence of a person and/or vitality signs to locate for example the mouth of a person which is speaking and generate data inputs to detect one or more objects location in the vehicle. According to some embodiments, the processor 252 may further receive and/or generate additional data 279 including for example info on the vehicle state 278, speed and acceleration 277 as captured by vehicle sensors 273. The sensory data 282 and the additional data 279 are analyzed by the processor 252.

According to some embodiments, the sensory data 282 and the additional data 279 are analyzed using a multitude of computer vision and machine learning algorithms. These may include but are not limited to a Convolutional Neural Network detecting people, networks that specifically detect the face, hands, torso and other body parts, networks that can segment the image and specifically the passengers in the image based on the 2D and 3D images, algorithms that can calculate the volume of objects and people and algorithms that can determine if there is motion in a certain region of the car The analysis output multiple types of data on objects in the vehicle cabin, such as information on occupants or inanimate objects such as a box or bag of groceries or an empty child seat including for example. Specifically, in some cases the data may include: detected body parts of objects 289 and/or motion of objects 288 and/or volume of objects 287 and/or occupancy state based on deep learning 286 in the vehicle cabin.

According to some embodiments, the multiple types of data may include depth data 294 including one or more depth images, obtained for example by the sensor 276. The depth data may be specifically used to detect body parts of the passengers and segment the body or body parts in the image. In some cases, the depth data may also be used to determine the pose of a person, such as sitting up-right, leaning to the side or leaning sideways.

According to some embodiments, the multiple types of data may include prior knowledge 292.

Nonlimiting examples of prior knowledge may include: information on the vehicle units such as doors/window/seatbelt state and/or prior information on objects and/or passengers in the vehicle; and/or rules or assumptions such as physical assumptions or seat transition rules relating to likelihood of movements inside the vehicle, for example, to rule out unlikely changes in the occupancy prediction or alternatively confirm expected changes in the vehicle occupancy state. Specific examples of the physical assumptions may include for example a high probability that the driver seat is occupied in a driving vehicle (nonautonomous vehicle) and/or low probability that a passenger may move to one of the rear seat in a predetermined short time, or from one seat to another seat in a single frame.

At the following step 293 the multiple types of data is fused to determine at step 294 the number of seat occupancy and/or object (e.g. passenger) such as objects 271 and 272 position and attribution (e.g. whether a passenger is sitting straight, leaning to the side or forward) are detected and/or identified. For example, the detection may include identifying one or more passengers, such as a complete body or body portion such as a face or hand at the rear section of the vehicle.

According to one embodiment, the multiple types of data are fused by a fusion algorithm which outputs the best decision considering the reliability of each data input (e.g. the motion of objects 288 and/or volume of objects 287 and/or occupancy state based on deep learning 286 face detection 290 prior knowledge 292).

Specifically, the fusing algorithm includes analyzing the fused data to yield a stochastic prediction model (e.g. Markov chain, for example in the form of a Markov matrix) of one or more predicted occupancy states probabilities. The prediction model is used to continuously update over time the probability of one or more current occupancy states (e.g. probability vector) to yield an updated occupancy state, e.g. determine in real time the location of objects 271 and 272 and/or the number of objects in the vehicle cabin. In some cases, the predicted state and the current state are combined by weighting their uncertainties using for example Linear time-invariant (LTI) methods such as Infinite impulse response (IIR) filters. Once the body or body parts are detected, the objects are tracked at step 295. For example, the objects may be tracked in the 2D image or the depth image using conventional trackers such as correlation trackers and edge trackers.

According to one embodiment, based on determined occupancy state the processor 252 may output at step 295 data or signals which may be used to provide information and/or for controlling devices, which may be remote or integral to the vehicle, for example, an electronic device such as an alarm, alert or a lighting may alert on out-of-position and accordingly activate an occupant protection apparatus (e.g. airbag) or other devices. The device may be controlled, such as activated or modulated, by the signal output according to embodiments.

In some cases, the output signals may include seat belt reminder (SBR), out of position indication (OOP) for example for airbags suppression and driver monitoring system (DMS) for driver's alert.

Alternatively or in combination, once the objects are identified using a neural network, then the neural network is trained to output a number of points such as a predefined number of points corresponding to certain body parts or a skeleton of lines. At the following step, these points and lines can be tracked in time using conventional tracking algorithms such as Kalman filters. It is stressed that the location of these points may be estimated by the tracker even if the tracking is lost, for example when the full body or parts of the body are obstructed, i.e. by the front seats.

According to some embodiments, the body parts of the passengers may be detected using computer vision algorithms and/or neural networks that are trained to detect persons such as human contour, for example, a complete human body and/or specific human body parts. Specifically, the face of a person may be detected by well-known detection or recognition methods. Non-limiting examples of such methods include Viola-Jones algorithm or SSD neural networks. Body parts may be detected by a neural network that is specifically trained to detect the body pose. Non-limiting examples of such methods include OpenPose or OpenPose Plus methods.

Figure 2C:
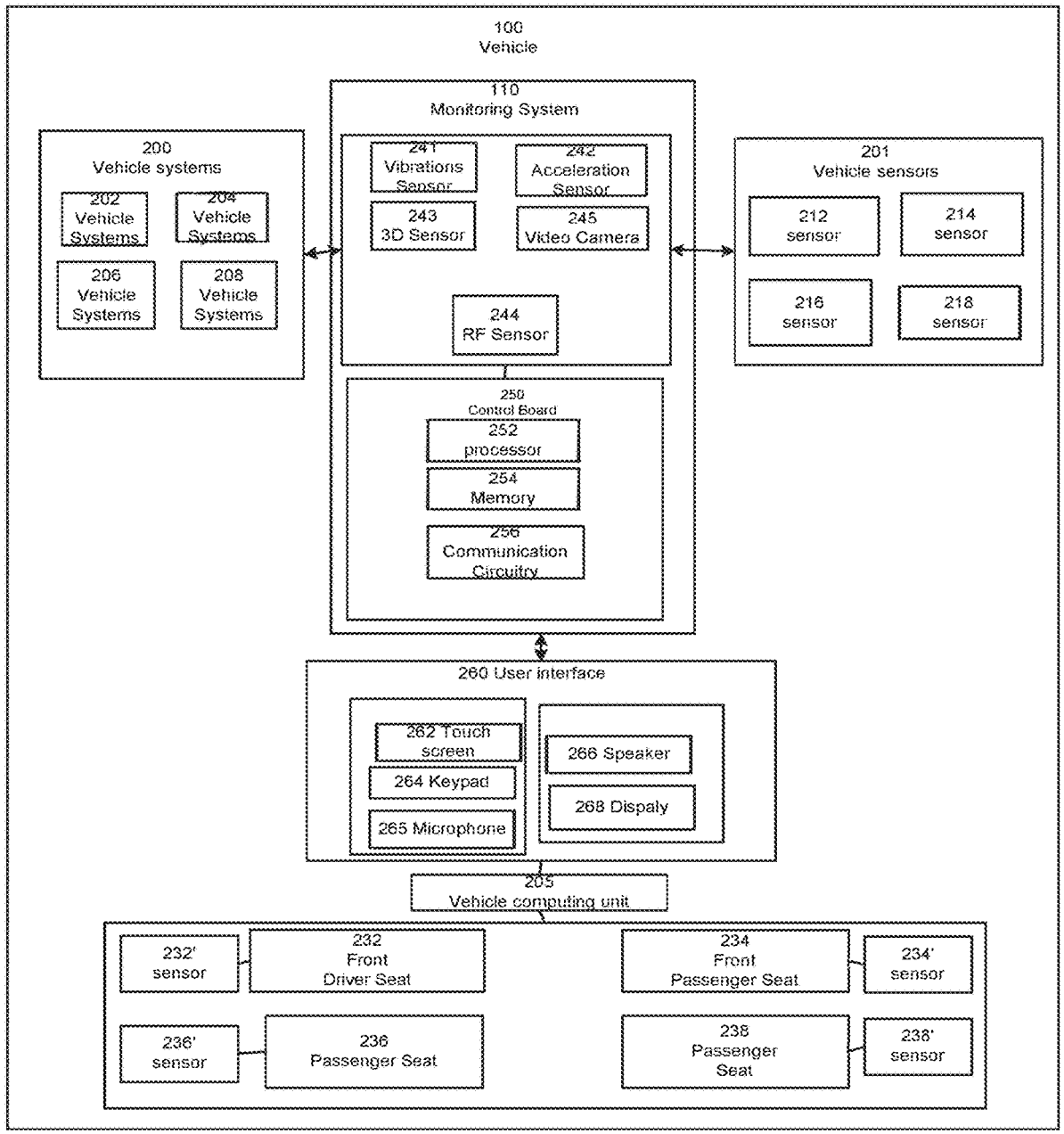
FIG. 2C illustrates a more detailed block diagram of the vehicle comprising the monitoring system, in accordance with some embodiments of the present disclosure.

FIG. 2C illustrates a more detailed block diagram of the vehicle 100. Notably, the vehicle 100 can include more or less components than those shown in FIG. 2B. For example, the vehicle 100 can include a wired or a wireless system interface, such as a USB interface or Wi-Fi, interfaces to connect the sensing system 110 and the vehicle's computing unit 205 with vehicle systems 200 such as vehicle systems 202-208, vehicle sensors 201 such as vehicle sensors 212-218 seat locations 232-238 and respective seat sensors 232'-238'. The hardware architecture of FIG. 2B represents one embodiment of a representative vehicle comprising a sensing system 110 configured to monitor and identify automatically objects and areas in the vehicle, such as hidden objects. In this regard, the vehicle of FIG. 2C also implements a method for monitoring objects and/or passenger to identify the attributes of the objects and/or passengers also in cases where due to momentary poor visibility or false detection they may not be identified. The identification may be based on various types of information received, for example in real time, from various types of sensors in the vehicle such as dedicated sensors embedded in the sensing system 110 and existing vehicle sensors embedded in various locations in the vehicle 100.

As shown in FIG. 2C, the vehicle 100 includes a vehicle computing unit 205 which controls the vehicle's systems and sensors and a sensing system 110 including a control board 250, which controls the sensing system 110 and which may be in communication with the vehicles units and systems such as the vehicle computing unit 205 and the vehicle systems 200. In some cases, the control board may be included in the computing unit 205. Vehicle 100 also comprises passenger seat position 232-238 including a driver's seat position 232, a front passenger seat position 234, and left and right rear passenger seat positions 236 and 238. Although four seat positions are shown in FIG. 2B for illustrative purposes, the present invention is not so limited and may accommodate any number of seats in any arrangement within the vehicle. In one implementation, each passenger seat position has automatically adjustable settings for seat comfort, including but not limited to, seat height adjustment, fore and aft adjustment position, seatback angle adjustment. Each passenger seat position may also include respectively and separately configurable one or more sensors 232'-238' for controlling the passenger's seats and windows and environmental controls for heating, cooling, vent direction, and audio/video consoles as appropriate. In some cases, the passengers may have communication devices 242-248, one for each passenger position, indicating that each passenger in vehicle 100 is carrying a communication device. Although the exemplary embodiment illustrated in FIG. 2C shows each passenger carrying a communication device, various implementations envision that not all passengers need to carry a device.

According to one embodiment, the sensing system 110 may include a plurality of sensors of different modalities. For example, the sensing system 110 may include a vibrations sensor 241, and/or an acceleration sensor 242, and/or 3D sensor 243, and/or an RF sensor 244, and/or a video camera 245, such as a 2D camera.

In some cases, the sensing system may include an image sensor for mapping a speckle field generated by each spot formed on the vehicle surface and a light source, such as a coherent light source adapted to project a structured light pattern, for example, a multi-beam pattern on the vehicle cabin. In accordance with embodiments a processor, such as processor 252 is configured to process speckle field information received by the image sensor and derive surface vibration information to identify one or more objects in the cabin, including for example motion and micro-vibrations of one or more of the detected objects.

The projected structured light pattern may be constructed of a plurality of diffused light elements, for example, a dot, a line, a shape and/or a combination thereof may be reflected by one or more objects present in the scene and captured by an imaging sensor integrated in the unified imaging device.

According to some embodiments, the control unit 250 may be connected to the vehicle systems 202-208, the vehicle's sensors 110, the sensing system sensors, the seat 232-238 and/or the seat's sensors' 232'-238' via one or more wired connections. Alternatively, control unit 250 may be connected to the vehicle systems 202-208, the vehicle's sensors 110, the sensing system sensors, the seat 232-238 and/or the seat's sensors' 232'-238' through a wireless interface via wireless connection unit 252. Wireless connection 252 may be any wireless connection, including but not limited to, Wifi (IEEE 802.11x), Bluetooth or other known wireless protocols and/or.

In accordance with embodiments, the computing unit 205 is also preferably controllably connected to the vehicle systems 202-208, the vehicle's sensors 110, the sensing system sensors, the seat 232-238 and/or the seat's sensors' 232'-238'. Vehicle systems 222-228 may be connected through a wired connection, as shown in FIG. 2, or by other means.

The vehicle systems may include, but are not limited to, engine tuning systems, engine limiting systems, vehicle lights, air-condition, multimedia, GPS/navigation systems, and the like.

The control board 250 may comprise one or more of a processor 252, memory 254 and communication circuitry 256. Components of the control board 150 can be configured to transmit, store, and/or analyze the captured sensory data, as described in further detail herein.

The control unit may also be connected to a user interface 260. The user interface 260 may include input devices 261, output devices 263, and software routines configured to allow a user to interact with the control board. Such input and output devices respectively include, but are not limited to, a display 268, a speaker 266, a keypad 264, a directional pad, a directional knob, a microphone 265, a touch screen 262, and the like.

The microphone 265 facilitates the capturing of sound (e.g. voice commands) and converting the captured sound into electrical signals. In some cases, the electrical signals may be used by the onboard computer 104 interface with various applications 352.

The processor 252 may comprise a tangible medium comprising instructions of a computer program; for example, the processor may comprise a digital signal processing unit, which can be configured to analyze and fuse data such as sensory data received from the various sensors using multiple types of detection methods. In some cases, the processed data output can then be transmitted to the communication circuitry 256, which may comprise a data encryption/transmission component such as Bluetooth™. Once encrypted, the data output can be transmitted via Bluetooth to the vehicle computing unit and/or the vehicle user interface and may be further presented to the driver on the vehicle. Alternatively or in combination, the output data may be transmitted to the monitoring unit interface.

FIG. 3A shows a schematic diagram of a sensing system 310, configured and enabled to capture sensory data of a scene such as a vehicle cabin 320, including one or more occupants (e.g. driver 311 and/or passenger 312) and analyze the sensory data to estimate the medical condition of the one or more occupants, for example following an accident of the vehicle, in accordance with embodiments. In some cases, the sensing system 310 may be the system 110 of FIGS. 1A and 1B.

System 310 includes a sensing module 300 and a control module 315. The two modules can reside in the same package or can be separated into two different physical modules. As an example, for a split configuration, the sensing module 300 can reside in the ceiling of the car, while the control module 315 can reside behind the dashboard. The two modules are connected by communication lines and/or may be in communication electrically and/or wirelessly for example through a dedicated connection such a USB connection, wireless connection or any connection known in the art.

In one embodiment, the sensing system 310 is connected to the vehicle's power. In an alternative embodiment, system 310 comprises a battery, optionally chargeable battery which allows operation even when the vehicle's power is down. Such a design would allow the system to keep operating even if the vehicle power fails during an accident. In a further embodiment, the battery is chargeable from the car's battery or from the car's alternator.

The sensing system 310 may also be equipped or has an interface to an impact sensor 325 configured to detect an imminent crash. A non-limiting example of such impact sensor is the impact sensor that exists in cars and is responsible for airbag deployment. In such a configuration, the notification of an impact is being transferred to the system 310 by an electronic signal from the impact sensor. The electronic signal may be transferred directly or by a communication system such as a vehicle's CAN bus interface. In some cases, the impact sensor may be or may be included in CAS as mentioned herein with respect to FIG. 1A.

Alternatively or in combination, the sensing system 310 is equipped with a built-in impact sensor such as an accelerometer 312. When an acceleration (or rather a deceleration) above a certain threshold is detected, the system 310 considers the impact signal as being provided, and that a collision will soon occur.

In another embodiment, an impact may be determined by analyzing data captured from the in-cabin vehicle, for example using the sensing module 300. As an example, the system 310 can monitor the video motion of the driver, passenger and objects in the cabin. When rapid or hectic movement is detected, beyond a predefined threshold, the system concludes that an impact is occurring. Such analysis can be based on computer vision algorithms such as, but not limited to, optical flow or tracking.

In accordance with embodiments, the sensing module 300 comprises an image sensor 301 and at least one illuminator 303 which can be configured to capture the sensory data including one or more images of the scene (e.g. car cabin) and further transmit the visual data to extract visual data, depth map(s) (e.g. density depth map(s)) and vibrations (e.g. micro-vibration data) of the scene using the control module as described in further detail herein.

The image sensor 301 is equipped with a lens 302. The lens can be a fish-eye lens covering the entire cabin. The illuminator 303 creates a light pattern illuminating the scene 320. The light pattern can be optionally designed to cover approximately the same field of view as the image sensor.

The image sensor 301 can be a CMOS or CCD sensors of various formats of resolution. For example, it can be a VGA format (640×480 pixels), or a 2 MPixel format (1920×1080).

In order to create the illumination pattern, the illuminator 303 may include a light source 324 that may be, as an example, a coherent laser light source. The illuminator 303 may also be equipped with a pattern creation optics, which may be as an example, a diffractive optical element (DOE) 326. Other examples for pattern creation may be a mask, or splitting mirrors and diffuser.

The light source 324, for instance, may include electromagnetic energy of wavelengths in an optical range or portion of the electromagnetic spectrum including wavelengths in a human-visible range or portion thereof (e.g., approximately 390 nm-750 nm) and/or wavelengths in the near-infrared (NIR) (e.g., approximately 750 nm-1400 nm) or infrared (e.g., approximately 750 nm-1 mm) portions and/or the near-ultraviolet (NUV) (e.g., approximately 400 nm-300 nm) or ultraviolet (e.g., approximately 400 nm-122 nm) portions of the electromagnetic spectrum. The particular wavelengths are exemplary and not meant to be limiting. Other wavelengths of the electromagnetic range may be employed. In some embodiments, the illuminator 303 wavelength may be any one of about 830 nm, about 840 nm, about 850 nm, or about 940 nm.

In a particular embodiment, the illumination is performed in the near infra-red (NIR, about 750-1400 nm) spectral range, in order to prevent the pattern from being visible to the naked eye of an occupant.

In some cases, the image sensor 301 can be equipped with a band-pass spectral filter preventing it from capturing light in wavelengths not matching those of the illuminator. When such a band-pass filter is added to the image sensor 301, the signal to background ratio improves.

In some aspects of the embodiments, both the image sensor 301 and the illuminator 303 (e.g. the sensing module 300) are connected to or may in communication with one or more processors such as processor 304 located in the control module 315.

In several embodiments, the processor 304 may operate the illuminator 303 and the image sensor 301 according to a monitoring policy. As an example, the processor 304 can operate the image sensor 301 at a frame rate of 30 frames per second (FPS) and the illuminator 303 as a constant light source. As another example, the processor 304 can operate the image sensor 301 at 30 FPS and the illuminator 303, alternatively, may be obtained only every second frame with a pattern, while the remaining frames are without a pattern. For example, one option may include capturing a clean frame (e.g. which does not include reflected pattern) and then one patterned frame. Alternatively, capturing 5 clean frames and then one pattern frame and etc. The later mode may be desirable as it may be advantageously used in order to obtain alternatively clean image frames for deep learning algorithm, and also pattern frames that can be used for vibration monitoring and vital signs extraction. Other option including a different relation between the number of pattern frames and clean frames may be used.

In an embodiment, the processor 304 is configured to extract any one or more or a combination of images such as video images, depth data and vibration data from the video stream.

In an embodiment, extracting video images is performed by selecting video frames in which the illumination source 324 was off and no light pattern was projected onto the scene. In another embodiment, the video images can include the light pattern created by the illuminator.

In an embodiment, extracting depth data is performed by using a structured light technique. The light pattern induced by the illuminator 303 is captured by the image sensor 301. The processor 304 is configured to receive the captured images and analyze the captured images to identify the displacement of each of the pre-known light pattern elements thereby calculating the depth of the object at this location.

The depth can be estimated for each pattern element by using the formula in equation 1 below:

$$z = \frac{Bf}{\Delta},$$ Equation 1 where z denotes the depth estimation, B denotes the baseline distance between the image sensor and the pattern illuminator, f denotes the camera module lens's focal length, and Δ denotes the disparity, i.e. the distance in which the pattern element has shifted across the image plane.

Alternatively or additionally, the depth can also be obtained by employing a look-up table mechanism. To employ such a mechanism, the system needs to undergo a calibration process in which the light pattern is projected onto a screen positioned at several predefined distances. For each distance, the pattern is recorded and stored in memory such as memory module 305. Then, for each small region that includes some light pattern element observed by the camera during operation, a correlation-based algorithm is employed to asses at which screen distance the closest matching pattern element occurs. The distance in which the correlation is the highest is chosen as the estimated distance for this region.

It is noted that the number of extracted depth points need not match the number of pixels in the image. Rather, it is related to the light pattern induced by the illuminator. In accordance with embodiments, the number of depth points is defined by the number of distinct light pattern elements in the projected pattern. As an example, this can be the number of spots, in a pseudo-random spot pattern, or a small factor of this number resulting from using a cluster of 2-3 points as the distinct pattern.

In another exemplary embodiment, the processor 304 is also configured to extract vibration such as micro-vibration information from the scene. The extraction of the micro-vibration is performed by analyzing the speckle content of at least some of the light (e.g. spots) pattern elements in the captured images. The changes over time of the speckle pattern can be indicative of micro-vibrations, i.e. very small and subtle movements that may be too minor to be detected by analyzing variations in the depth data or in the video images which do not include the light pattern elements.

In some embodiments, the speckles pattern analysis may include detecting the changes to the speckle pattern by measuring a temporal standard deviation in the intensity of the respective reflected diffused light element over multiple consecutive captured images to identify a temporal distortion pattern. For example, assuming $I_i$ is the gray level intensity of a certain pixel depicting light pattern element and/or a part thereof in an image number i, one or more processors such as processor 304 may calculate the temporal standard deviation according to equation 2 below.

$$S_n = \sum_{i=n-k}^{n} I_i^2 - \left(\sum_{i=n-k}^{n} I_i\right)^2$$ Equation 2 where n denotes the current image and k denotes the number of previous images.

The analysis may further include comparing the result of the temporal standard deviation to a predefined threshold value to determine whether a micro-vibration occurred. In case the temporal standard deviation value exceeds the predefined threshold, it is determined, for example by the processor 304, that the magnitude of the micro-vibrations in the specific light pattern element increased. On the other hand, in a case where the temporal standard deviation value does not exceed the predefined threshold, the processor 304 may determine that there is no change in the magnitude of the micro-vibrations. In certain embodiments, the predefined threshold value may be fixed and set in advance. Optionally, the predefined threshold value can be dynamically adjusted according to the value of the temporal standard deviation measured over time.

Optionally, in order to improve immunity to noise which may affect the intensity level of the speckle pattern and increase the Signal to Noise Ratio (SNR) of the intensity of the speckle pattern, the temporal standard deviation may be averaged over multiple pixels (e.g. 5×5 pixels) of each spot.

Optionally, in order to improve immunity to noise which may affect the intensity level of the speckle pattern and increase the Signal to Noise Ratio (SNR) of the intensity of the speckle pattern, the temporal standard deviation may be averaged over multiple speckle patterns of diffused light elements reflected from the same surface and portrayed in the same region in the captured images.

According to another embodiment, the changes to the speckle pattern may be detected, for example by the processor 304, by analyzing the speckle pattern for lateral translation which is indicative of a tilt of the reflecting object with respect to the image sensor. The tilt which may be very minor, for example, on a scale of micro-radians, may be derived from the translational velocity of one or more speckle pattern point(s) over time (consecutive frames). The lateral speckle pattern translation may be derived from analysis of the diffused light pattern element(s) depicted in a plurality of consecutive captured images according to equation 3 below.

$$v = \frac{\frac{dI}{dt}}{\frac{dI}{dx}}$$
Equation 3 where I denotes the intensity of the pixel in the captured image in gray level differentiated with respect to a time t or position x.

The angular velocity in a change of a certain pixel (i, j) with respect to its neighboring pixels in the i direction in captured image n may be expressed by equation 4 below.

$$vi_{i,j}^n \approx \frac{I_{i,j}^n - I_{i,j}^{n-1}}{I_{i+1,j}^n - I_{i-1,j}^n}$$
Equation 4

The angular velocity in a change of a certain pixel (i, j) may be expressed similarly in the j direction. The result of the angular velocity is expressed in pixel per frame units.

Optionally, the intensity $I_{i,j}$ of the pixel (i, j) over time to be normalized, for example by the processor 304, to compensate for non-uniformity in intensity $I_{i,j}$ due to spot intensity envelope effects. For example, the intensity $I_{i,j}$ may be normalized by applying a sliding temporal window for averaging the intensity $I_{i,j}$ of one or more pixels (i, j) in the consecutive captured images. In another example, the processor 304 may smooth the intensity $I_{i,j}$ in the time domain by applying an infinite impulse response to the $I_{i,j}$ to produce a smoothed intensity $\bar{I}_{i,j}$ as expressed in equation 5 below.

$$\bar{I}_{i,j} = \alpha I_{i,j}^n + (1-\alpha)\bar{I}_{i,j}$$
Equation 5:

where α denotes a small factor, for example, 0.05.

The intensity $I_{i,j}$ of one or more of the pixels (i, j) may be normalized by dividing it with the average intensity measured over time in a plurality of consecutive captured images to produce a normalized intensity $\hat{I}_{i,j}^n$ as expressed in equation 6 below.

$$\hat{I}_{i,j}^n = \frac{I_{i,j}^n}{\bar{I}_{i,j}}$$
Equation 6

Replacing the expression of the intensity $I_{i,j}^n$ in equation 4 with the normalized intensity $\hat{I}_{i,j}^n$, the angular velocity may be expressed by equation 7 below.

$$vi_{i,j}^n \approx \frac{\hat{I}_{i,j}^n - \hat{I}_{i,j}^{n-1}}{\hat{I}_{i+1,j}^n - \hat{I}_{i-1,j}^n}$$
Equation 7

In some embodiments, in order to further improve the robustness of the measured intensity against noise effects, the processor 304 may further spatially average the intensity over multiple adjacent reflected diffused light elements (e.g. dots, spots, etc.) in the captured images. The processor may further apply temporal filtering over the spatially averaged intensity value to improve the resulting intensity signal.

Further details on the speckle pattern analysis for detecting the micro-vibrations may be found in U.S. Pat. No. 10,345,137 entitled "System and Method for Detecting Surface Vibrations", and PCT International Application Publication Number WO2019012535 entitled "Systems and methods for acquiring information from an environment", each of which are incorporated herein by reference in their entirety.

It is noted that depth data and vibrations (e.g. micro-vibration) can be extracted from the captured images separately or together (e.g. simultaneity), according to the configuration of the processor 304.

In some cases, the processor 304 may also analyze the extracted depth data and vibrations (e.g. micro-vibration) and captured visual data to provide medical information including an analysis of the medical status such as injury related status of the one or more occupants in the vehicle. In some cases, the medical information is provided in real-time or close to real-time. In certain embodiments, the processor analyzes post-crash vital-signs, pose, and injury severity as described in further details herein.

According to various aspects and embodiments, the processor 304 is connected to or may be in communication with a memory module 305. The memory module is configured to store data such as 2D data (e.g. visual images) and/or 3D data and/or vibrations during analysis. It may also store pre-crash data to be retrieved in case an accident occurs. In some cases, the memory module 305 may receive data from internal units in the vehicle such as the vehicle's computer device and/or memory units and/or from external devices such as mobile phone devices.

The processor 304 may be connected to or may be in communication (e.g. wirelessly) with a communication module 306 in order to communicate the results of the analysis (e.g. the medical data) to the external world. In some cases, the results can be transmitted to a cloud based storage system 307 or to a rescue team 309.

In many embodiments, the sensing system 310 may be in wireless communication 116 with the cloud-based storage system 307. In some cases, the system can transmit the data to a mobile device 350 using communication module 306 with a communication link, such as a wireless serial communication link, for example, Bluetooth™. The hand held device can receive the data from the system and transmit the data to a back end server of the cloud based storage system 307

The transmitted data can be structured in the form of a message including information such as the position or status of one or more occupants inside the post-crash vehicle. In an embodiment, the transmitted data can also include images or video sequences form the sensor.

In accordance with embodiments, the estimation of the post-crash medical condition of a vehicle occupant can be performed based on any combination of the pre-crash data, during-crash data and post-crash data as described in further details herein.

FIG. 3B shows a schematic diagram of a sensing system 370, configured and enabled to capture sensory data of a scene such as a vehicle cabin 320, including one or more occupants (e.g. driver 311 and/or passenger 312) and analyze the sensory data to estimate the medical condition of the one or more occupants, for example following an accident of the vehicle, in accordance with embodiments.

System 370 presents all elements of the aforementioned system 310 but further includes a number of sensors such as an image sensor 372, a depth sensor 374, for example, a stereoscopic camera and a micro-vibration sensor 376.

Figure 4:
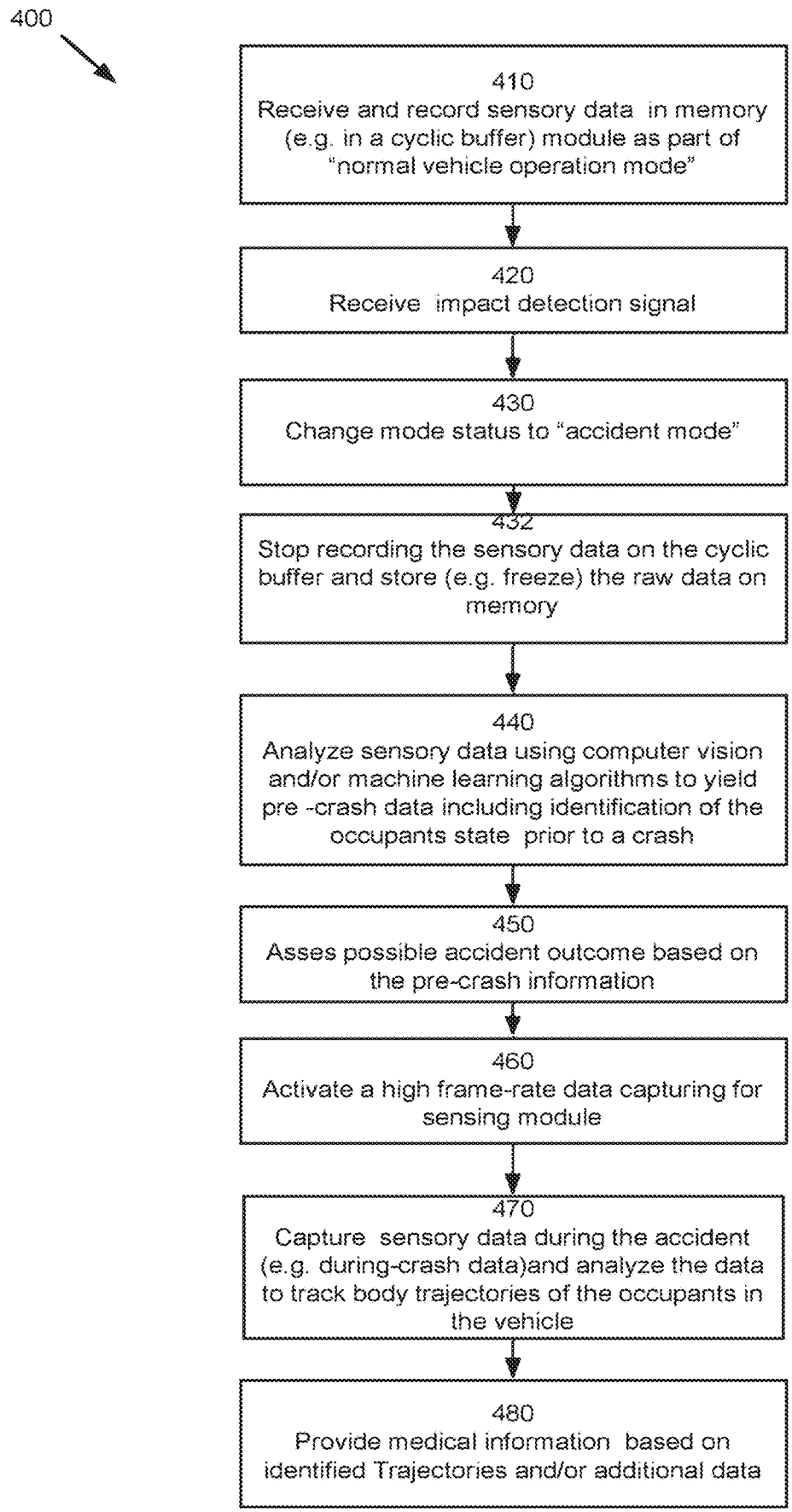
FIG. 4 shows a flowchart for capturing and processing in-cabin data, in accordance with some embodiments of the present disclosure.

FIG. 4 shows a flowchart of a method 400 for capturing and processing in-cabin data including pre-crash data, during-crash data and post-crash data to provide information such as medical information following or during a vehicle accident, in accordance with embodiments. At step 410, during normal vehicle operation, a system such as system 110 of FIGS. 1A-1C or system 310 of FIG. 3A receives and records data such as captured sensory data (e.g. raw data-defined as primary data collected from one or more sensors such as the sensors in the sensing module) of the in-cabin vehicle. In accordance with embodiments, the sensory data may be captured by the sensing module 300 and may include any one or more of the video images, depth data, and vibration data. In some cases, the captured sensory data may be stored using, for example, a buffer such as buffer 301. In some cases, the buffer 301 may be a cyclic buffer comprising, for example, a storage capability of 10 seconds length, 20 seconds length, or more. The term "cyclic" as used herein refers to a fixed amount of memory that is used to store the data captured in an amount of time, such that when the memory has been filled, the old data is overwritten by new data in a cyclic manner.

In some cases, the sensory data may include vehicle internal data obtained from the vehicle units such as the vehicle embedded sensors.

At step 420 an impact detection signal may be received for example at the control module. In some cases, the impact detection signal may be generated by the impact sensor 325 and/or the processor and/or sensing module following an imminent crash detection. In some cases, the impact detection is obtained from the vehicle embedded sensors such as the CAS or other sensing modules.

A non-limiting example of such impact sensor is the impact sensor that exists in cars and is responsible for airbag deployment. In such a configuration, the notification of an impact is being transferred to the system by an electronic signal from the impact sensor. The electronic signal may be transferred directly or by a communication system such as vehicle's CAN bus interface. In another embodiment, the system is equipped with a built-in impact sensor such as an accelerometer as mentioned above. When an acceleration (or rather a deceleration) above a certain threshold is detected, the system considers the impact signal as being provided. In another embodiment, the impact case is analyzed from the system data. As an example, the system can monitor the video motion of the driver, passenger and objects in the cabin. When rapid or hectic movement is detected, beyond a predefined threshold, the system concludes that an impact is occurring. Such analysis can be based on computer vision algorithm such as, but not limited to, optical flow or tracking.

In some cases, at step 430, once an impact detection signal is received, for example from the impact detection sensor 302, the system mode changes from "normal vehicle operation mode" to "accident mode". In accordance with embodiments, as part of the "accident mode" the system operates one or more actions as follows: at step 432 the recording on the cyclic buffer 301 is stopped and the raw data (e.g. sensory data) contained in the buffer is "frozen" in memory 303 for further analysis.

Optionally or in combination, the sensory data can also be transmitted to external sources such as the cloud based memory units 307 located at emergency agencies such as the police, hospital, etc., for advanced crash investigations. The transmission can happen during the crash or at a later stage when an investigation is initiated.

In an embodiment, the details of the impact as identified for example by the processor may also be recorded by the processor. Such details can include the magnitude and/or the direction of the impact. These details can then be used to asses the results of the accident.

At step 440 the sensory data stored at the buffer is analyzed, for example by the processor, to yield pre-crash data including for example identification of the vehicle's occupants state prior to the crash (e.g. pre-crash state), in accordance with embodiments. Such analysis can provide any combination of the position of the occupant, the body pose, the body attributes such as mass, height, age, gender and body type. The analysis can also include objects that exist inside the cabin and can pose injury risks during an accident.

The analysis described herein can be performed using computer vision and/or machine learning algorithms. The position of an occupant is obtained by training a computer vision module to identify the existence of individuals inside the car. The body pose can be obtained by training a neural network system to estimate body pose from video images. Body attributes can be obtained by training a neural network to estimate the attributes from video images.

In an embodiment, the analysis can also be performed or be enhanced by the use of the depth data layer, providing information regarding the volume of an individual and its physical dimensions. The depth information can also provide information relevant to the body pose.

In an embodiment, the processor is configured to analyze one or more pre-crash depth maps to extract a body attribute including, such as mass, height, width, volume, age, and gender as illustrated in FIGS. 2B and 2C.

In an embodiment, the analysis comprises the use of a combination of at least one image and at least one depth map.

At step 450, following the pre-crash car occupant state identification at step 440, the system assesses the possible accident outcome in terms of injuries and medical issues based on the analyzed pre-crash data which included identification of the occupants' state prior to the accident, in accordance with embodiments.

In an embodiment, the system employs a human body mechanical model which can use the recorded pre-crash data, to assess the outcome of the vehicle crash in terms of injuries and medical issues. The available pre-crash information may include one or more or all of the vehicle occupants' body's attributes, body's initial pose, body mass, age, body dimensions, and gender and impact parameters such as magnitude and direction.

In some cases, the human body mechanical model might be a finite-element model of the body. Alternatively or in combination, the human body mechanical model can contain heuristic equation based on existing injuries databases.

In an embodiment, the system is triggered to initiate the analysis of the nature or severity of injury by utilizing vehicle impact sensors. In various embodiments, a vehicle impact sensor such as sensor 325 comprises a microswitch located inside the vehicle's bumper, the microswitch is configured to detect strong impacts. In an embodiment, the system uses the same sensors as the vehicle's airbag deployment system.

To illustrate possible considerations in such an assessment, the pre-crash head pose of the occupant 102 relative to the body is addressed. The whiplash effect during a car accident as illustrated in FIG. 1B can cause various types of injuries to the occupant's neck. Knowing the direction and magnitude of the impact as obtained, for example, as obtained from the impact sensor, and the head position and orientation relative to the body and to the car, as obtained and extracted by analyzing the captured images the system can provide a prediction as to the nature and severity of the injury. Specifically, the analysis may include identifying which body part got impact. Based on the nature of this body part and the estimated strength of the impact predict tissue damage, vascular damage, bone damage, etc.

In an embodiment, the system is configured to store pre-crash images. In additional embodiments, the system is further configured to send the pre-crash images and the pre-crash data to a first responders' team or to upload said images to a cloud service to be extracted by a first responders' team.

In an embodiment, the processor is configured to analyze one or more stored pre-crash images in order to extract a pre-crash body pose. In further embodiments, the processor is configured to analyze the pre-crash depth maps (e.g. body pose), optionally in combination with any available information regarding the physical parameters of the impact, thereby providing an assessment of the nature or severity of an injury.

In an embodiment, the processor is configured to analyze one or more pre-crash images in order to extract at least one body attribute including, but not limited to, mass, height, width, volume, age, and gender. In some embodiments, the processor is further configured to use said at least one body attribute, optionally in combination with any available information regarding the physical parameters of the impact, in order to analyze and assess the nature or severity of an injury.

In accordance with some embodiments, at step 460 once a detection of an impact (e.g. of step 420) is received, for example at the system (e.g. the processor) it may instruct the system's sensors such as the system sensing module to shift sensors and/or camera's operating mode to a high-frame rate capturing mode, such that a high-frame rate data will be collected during the occurrence of the accident. A non-limiting example for high-frame rate includes about 500 to 1000 frames per second or more. A non-limiting example of the duration of the accident occurrence includes about 1-5 seconds or more.

At step 470 the system is configured to capture data such as sensory data obtained during the accident (e.g. during-crash data), for example during the high frame-rate period, in order to follow the trajectories of the occupant(s) and object(s) inside the car. The system may use any of the captured video images and/or the depth data in order to analyze the trajectories using computer vision methods as known in the art. The trajectories are especially important in order to detect body impact with the vehicle's structure and various surfaces as well as to detect impact of occupants by objects in the vehicle.

At step 480 the trajectories and impact data are used to provide medical information output which includes an assessment and prediction of the nature and severity of injuries of the occupants. In some cases, the medical information output may be provided based on additional data including, for example, pre-cash data. As an example, detecting an impact between the occupant's head and the car's structure might indicate a high probability for head trauma. More specifically, as shown in FIG. 1A the data including the distance 'd' between the passenger 112 head and the front seat headrest 113 and the vehicle 100 speed during "normal vehicle operation mode" may be analyzed and combined with the passenger trajectory 118 and broken window 114 trajectory extracted from data captured during the vehicle 100 crash.

In some cases, the medical information output may be transmitted as one or more output signals to external units such as first responders units or to the vehicle's internal units to activate one or more devices or system, such as a vehicle's devices.

Figure 5A:
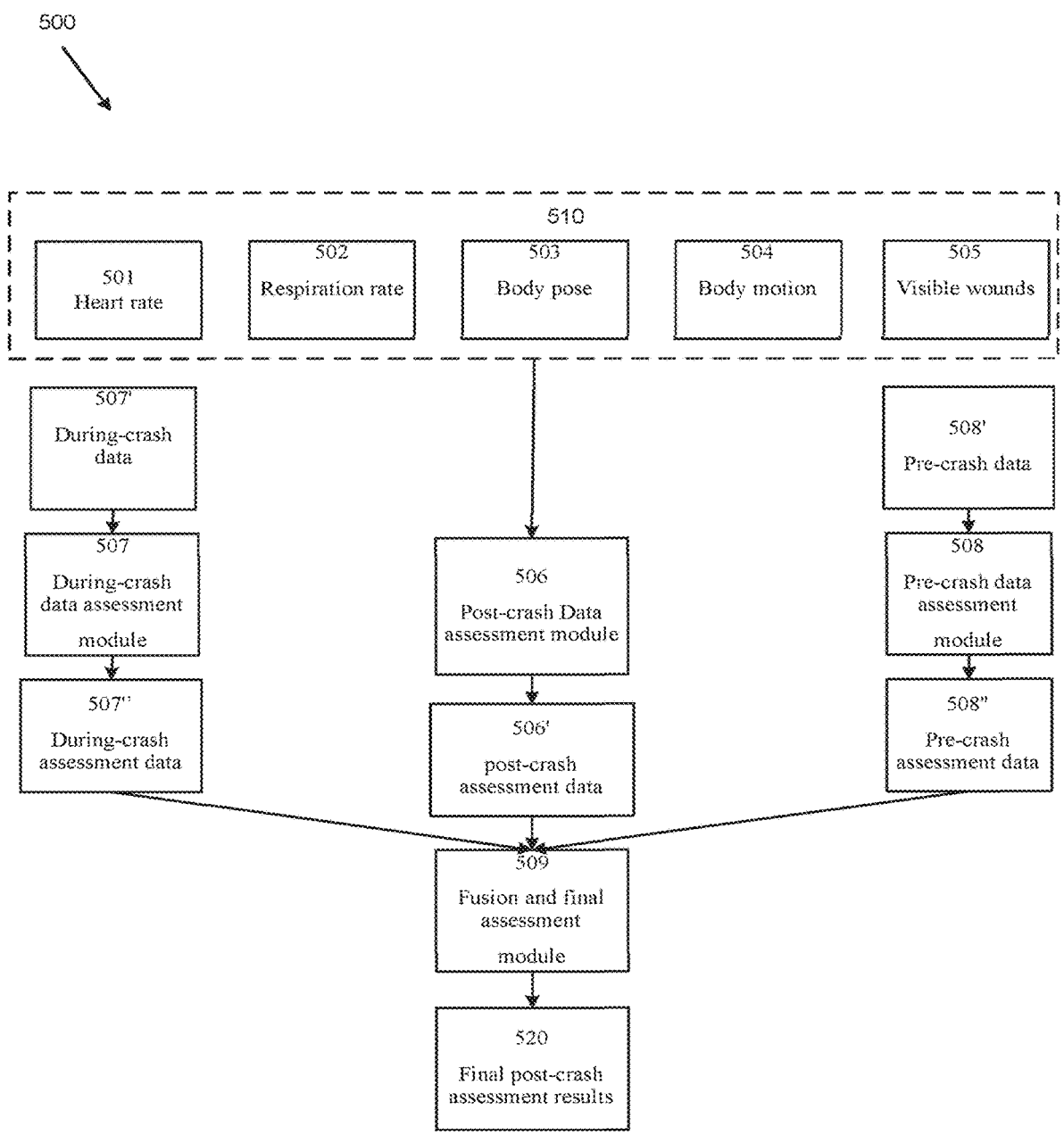
FIG. 5A shows a high-level block diagram of a vehicle post-crash data, during-crash data, and pre-cash data collection procedure, in accordance with some embodiments of the present disclosure.

Reference is now made to FIG. 5A which shows a high-level block diagram 500 of a vehicle post-crash data, during-crash data, pre-cash data collection procedure, in accordance with embodiments. The collection procedure may be carried out by a sensing system such as the sensing system 110 of FIG. 1 or sensing system 310 FIG. 3. In some cases, the system may be in communication or may include additional sensors. As schematically shown, the system 110 collects some or all of the information available in the vehicle cabin to produce medical information including an assessment of the medical condition status and injuries nature and severity of the occupants.

In accordance with embodiments, each type of captured information may be transformed to one or more signal including the related information.

In an embodiment, the system, such as system 110 may collect the occupants' heartbeat 501 by capturing and analyzing micro-vibrations of the body, such as one or more micro-vibrations signals obtained by the system 110 and analyzed by one or more processors. The micro-vibrations are captured using speckle temporal analysis as detailed hereinabove. The heartbeat causes skin mechanical micro-vibration due to the pulse, such micro-vibrations being detectable by the system 110 configured to measure micro-vibration. The heart-rate or lack of heartbeat provides crucial information regarding the medical condition status of the one or more occupants in the vehicle and the nature and severity of their injury.

In another embodiment, the system such as system 110 is configured to collect the occupants' respiration rate 502 by analyzing micro-vibration of the body, and specifically, of the chest area. The breathing motion causes micro-vibrations or vibrations that can be detected by system 110 which is configured to measure micro-vibrations. Breathing rate or lack of breathing provides crucial information regarding the medical status of the one or more occupants and the nature and severity of their injury.

In accordance with embodiments, both signals of heart-rate and raspatory rate can be obtained by analyzing post-crash bodily micro-vibration signals. In order to discriminate between the two signals, a spectral analysis may be employed. As an example, the micro-vibration signal may contain a superposition of a stronger raspatory signal and a weaker heart-rate signal. The heart signal may be of a typical range of 50 beats per minute (BPM) or more (~1-1.2 Hz), while the breathing signal may be of a typical range of 15-20 breaths per minute (~3-4 Hz). Thus, performing spectral analysis and separating signal in this example at about ~2 Hz into high-pass and low-pass, would allow obtaining the two separate signals.

In addition, the same spectral analysis can be used in another embodiment to discriminate between vital signs signals and mechanical vibrations resulting from the vehicle or environment. As an example, in a post-crash situation in which the engine of the car keeps running, it can be expected that there will be mechanical vibration associated with the working of said engine. Assuming the idle rotations per minute (RPM) of the engine is 600 RPM, this means a typical base frequency for the engine induced mechanical vibration of 10 Hz. By using a low-pass below this frequency, the engine induced vibration can be cleaned from the captured signals.

In an embodiment, the system is configured to also detect the post-crash body-pose 503. The system 110 can use some or all of the captured images and the depth data. The system then employs a skeleton model or other heuristics in order to estimate the body-pose. The body pose, and specifically the relative position and orientation of the head and limbs, can provide valuable information regarding the medical condition status and the nature and severity of an injury. In some cases, the occupant's body pose may be identified using systems and methods as described in USP application No. 62/806,840 entitled "SYSTEM, DEVICE, AND METHODS FOR DETECTING AND OBTAINING INFORMATION ON OBJECTS IN A VEHICLE" which is incorporated herein by reference.

In another embodiment, the system is configured to also use images such as video images and/or depth data in order to detect bodily motion 504 of the occupant(s). The detection can be performed by known computer vision algorithms such as, but not limited to, optical flow and visual tracking methods. For example, Lucas-Kanade optical flow algorithm in OpenCV. The detection of motion or lack of motion of the one or more occupants in the vehicle provides valuable information regarding the medical condition status and nature and severity of an injury of the one or more occupants.

In some cases, the system is triggered to initiate the analysis by visually detecting rapid hectic motion of an occupant inside the vehicle. An example for such a detection mechanism is based on optical flow algorithm configured to analyze the relative displacement of objects between two or more consecutive frames.

In another embodiment, the system is further configured to detect visual signs of body wounds 505 of the one or more occupants. An example of visually detectable wounds can be skin rapture or a fracture. One way to configure the system to detect wounds is by training a deep learning classifier to detect broken skin or bleeding, for example, by showing wounds images and training the classifier to recognize the wounds. In operation, captured images of the injured one or more occupants are obtained at the processor which operates a deep neural network to get a prediction and to detect and identify the type of injuries.

In accordance with embodiments, each type of captured information such as heartbeat 501 respiration rate 502 may be transformed into one or more signal including the related information.

In various embodiments, the conversion of the information to one or more signals may be performed either locally (with a processor and software supplied with the system) or remotely. Heavier calculations for more complicated analyses, for example, can be performed remotely.

In accordance with embodiments, all or some of the above-mentioned signals and assessments 510 are transmitted to a data assessment module such as single post-crash data assessment module 506. The collected data signals 501, 502, 503, 504, and 505 may be used together or separately. It is stressed that in some cases only some of the signals may be used as some of the signals were not received or due to some other desired configuration. For example, in some cases, only signals 501 and 502 may be received.

In accordance with embodiments, the post-crash data assessment module 506 is configured to fuse the different received signals, including the captured information, and process the received signals to yield a post-crash assessment data 506' including the medical condition of the vehicle's one or more occupants.

As an example, the assessment can include using a check list such as a binary check list including a question list comprising medical questions utilized to assess the medical condition of the occupants. the check list may include one or more of the following questions: weather there are pulse and breathing; and/or whether there are signs of consciousness; and/or whether there is suspicion for fractures and on which body part; and/or whether there is a suspicion for internal injury; and/or whether there is a suspicion for head injury; and/or whether there is an open wound or a suspicion for blood loss, etc. It is understood that embodiments of the present invention may use any other kind of diagnosing check lists or other methods to identify the medical condition of the occupants based on the captured data.

In accordance with embodiments, the system further comprises a pre-crash assessment module 508 configured to receive raw data (e.g. sensory data), such as pre-crash data 508' stored, for example at the buffer and analyze the raw data to yield pre-crash assessment data 508". The pre-crash assessment data 508" includes identifications of the pre-crash state of the vehicle's one or more occupants. Such analysis can include any combination of the position of the occupant, the body pose, the body attributes such as mass, height, age, gender and body type. The analysis can also include objects that exist inside the cabin and can pose injury risks during an accident.

In accordance with further embodiments, the system comprises a during-crash data assessment module 507 configured to receive store and analyze sensory data, such as during-crash data 507' captured during a vehicle accident to yield during-crash assessment data 507' including information which allows the system to follow the trajectories of the vehicle's occupant(s) and/or object(s).

The during crash assessment data 507", post-crash assessment data 506" and pre-crash assessment data extracted accordingly by modules 506, 507 and 508 are transmitted to a fusion module 509 configured to combine and processes the received data according to one or more fusing methods and logics to yield one or more final post-crash assessment results 520 relating to the medical status of the occupant(s).

An example of fusion logics used by the fusion module 509 includes a scenario where the system is configured to assess the likelihood of head trauma of one or more occupants in the vehicle cabin following an accident, in accordance with embodiments. The assessment process includes acquiring at the post-crash data assessment module 506 and one or more types of post-crash data 510 such as body pose 503 body motion 504 and the like, and analyzing the acquired post-crash data 510 in order to check if there are signs for injury in the occupant's head. In some cases, the system can then further use the during-crash data assessment module 507 to identify whether there was a head impact with car elements or other objects during collision based on received during-crash data. Such an impact would strengthen the likelihood of head trauma. If no head impact was detected during crash, and no head obstruction occurred, the likelihood of head trauma is reduced. Finally, the system may further obtain pre-crash data 508' at the pre-crash assessment data module 508 in order to analyze the position of the occupant's head relative to various car elements and yield pre-crash assessment data. Then, the pre-crash assessment data 508", during crash assessment data and post-crash assessment data 506" are fused at the fusion and final assessment module 509 to estimate the risk of head trauma. Specifically, the fusion estimation may be based on the direction and force of the external impact to the vehicle, using body modeling, module 509 can infer an increase or decrease the risk of head trauma.

It should be stressed that for head trauma type of injuries the analysis is mostly based on visual detection and classification of injuries.

It is also stressed that the fusion module 509 may provide a final assessment result 520 based on any partial and/or combination of the data available from the pre-crash data 508', during crash data 507' and post-crash data 510.

The fusion module 509 may include stochastic predication models (e.g. Markov chain, for example in the form of a Markov matrix) of one or more predicted states probabilities.

FIG. 1C shows an example of a final assessment result 122, structured in the form of a message, in accordance with embodiments. The message may include one or more of the following details:

Occupant initial position: Rear left
Occupants gender: Female
Occupants estimated age: 50-65
Occupants estimated mass: 60-75 Kg
Suspected injuries: Neck trauma, ribs, lower back
Post crash vital signs: HR:110BPM, Respirations per minutes: 70

Figure 5B:
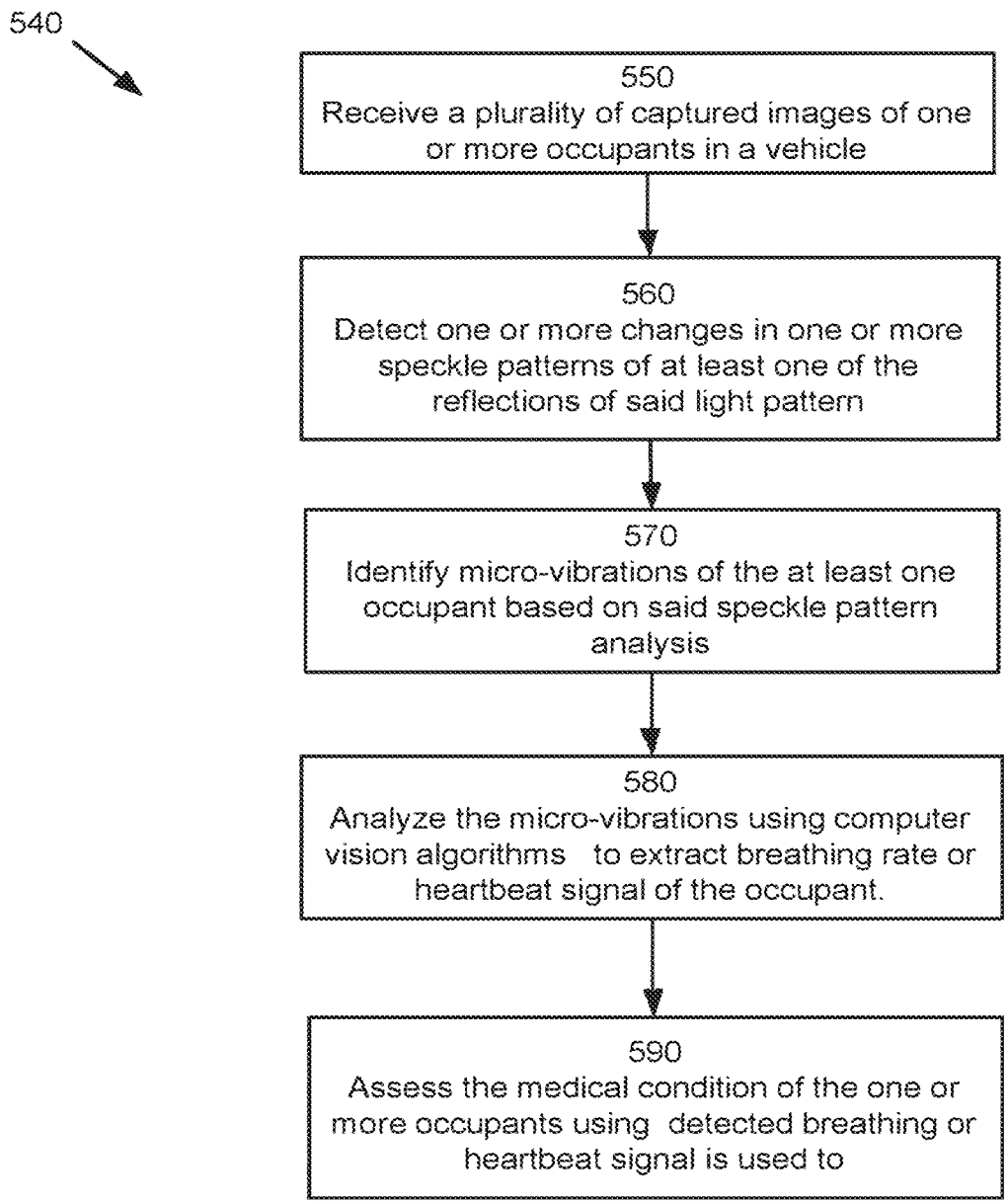
FIG. 5B shows a flowchart of a method for detecting the heartbeats and/or breathing of one or more occupants, in accordance with some embodiments of the present disclosure.

FIG. 5B shows a flowchart of a method 540 for detecting the heartbeats and/or breathing of one or more occupants, for example in a vehicle, by analyzing a plurality of captured images comprising reflected light pattern, in accordance with embodiments. According to an embodiment, the method comprises the following steps: at step 550 the plurality of images are received, for example from the sensing module at a processor. At step 560 one or more changes in one or more speckle patterns of at least one of the reflections of the light pattern are detected in at least some consecutive images of the plurality of images. At step 570 micro-vibrations of the at least one occupant based on the speckle pattern analysis are identified. At step 580 the micro-vibrations are analyzed using computer vision algorithms such as, but not limited to, optical flow or tracking to extract breathing rate or heartbeat signal of the occupant. Specific examples of the analysis method for extracting breathing rate or heartbeat signals of the occupant are illustrated in FIGS. 7A-7E and FIGS. 8A-8D. In some embodiments, the breathing or heartbeat signal is used to assess the medical condition of the occupant as shown in FIG. 5A. At step 590 the detected breathing or heartbeat signal is used to assess the medical condition of the occupant.

Figure 6:
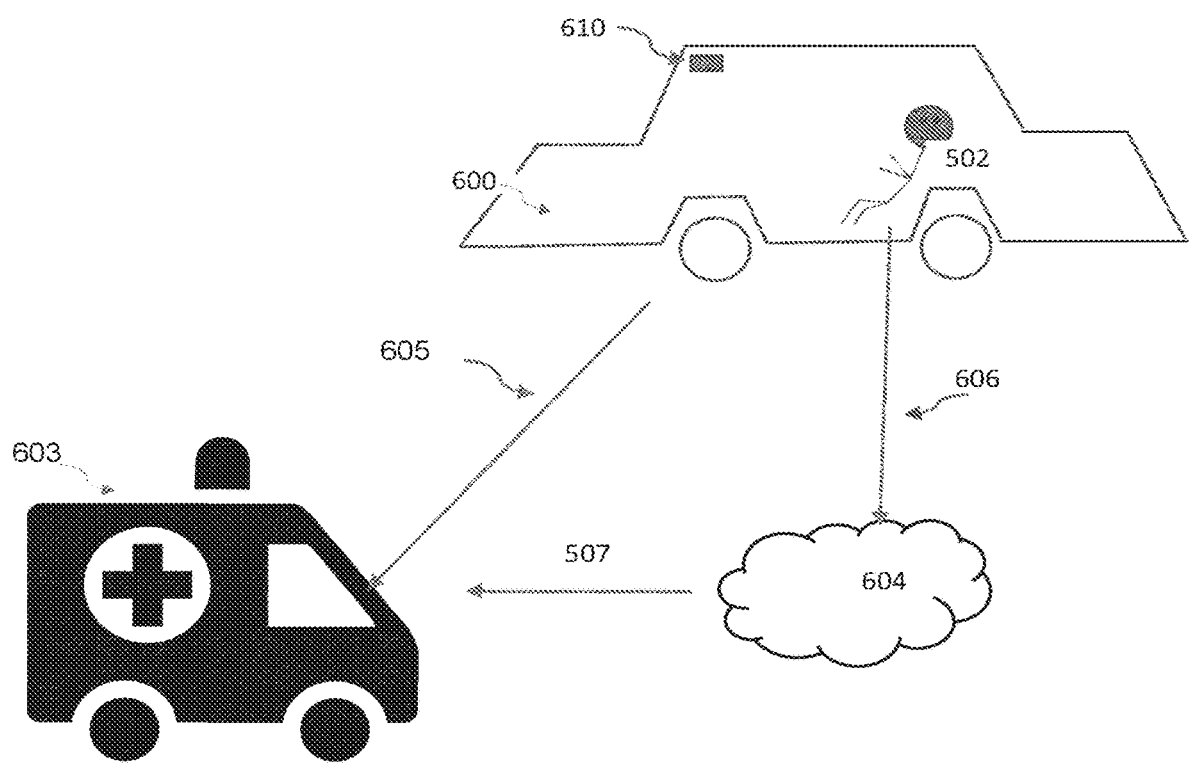
FIG. 6 shows a schematic of possible ways to handle the communication between the system and a first responders' team, in accordance with some embodiments of the present disclosure.

FIG. 6 illustrates two options in which the final post-crash assessment results 520, including for example the medical condition and injuries assessment provided in FIG. 5A, may be transmitted to an outsource responder unit such as first rescue responders, in accordance with embodiments.

In the first option, the assessment results 520 are transmitted directly from the system 610 in the vehicle 600 to the first responders 603 via a direct communication link 605. For example, the system 610 may broadcast one or more transmission signals including the assessment results 520 via a local wireless network to the first responders 603. Following the receipt of the signal, by logging into the local network, the first responders 603 can download the assessment results 520 which includes, for example, medical information regarding the in-cabin status of one or more of the vehicle's occupants.

In the second option, the system 610 may send data including for example the assessment results 520 to a cloud service 604 by a communication channel 606. The cloud service may be a virtual service that stores all the information from the system. Then, the first responders 603 can log into the cloud service and download the relevant information.

The main advantage of the second method over the first method is that the medical condition assessment data can be accessed even before arriving at the crash scene. This will allow sending the right first responders tools and vehicles to the scene.

In some cases, the cloud service can be also connected to treatment facilities such as hospitals to alert the medical team of the upcoming patients.

Another advantage of the cloud service is that it can receive partial data even if the system 601 does not survive the crash. In an embodiment, the pre-crash data 508' and during-crash data 507' may be sent to the cloud service as soon as they are generated. In this case, even if the system fails or may not be operated due to the crash, an assessment could be made based on the data available on the cloud.

Once the in-car medical assessment is available for the first responders it can be used to prepare the correct extraction procedure and the immediate treatment needed. The assessment can also help first responders to determine the priority of extraction and treatment in case of multiple casualties.

In another embodiment, the system can use the impact detection 302 of FIG. 4 in order to send an automatic alert to the local first responders' organization such as police, fire department and medical teams.

Figure 7A:
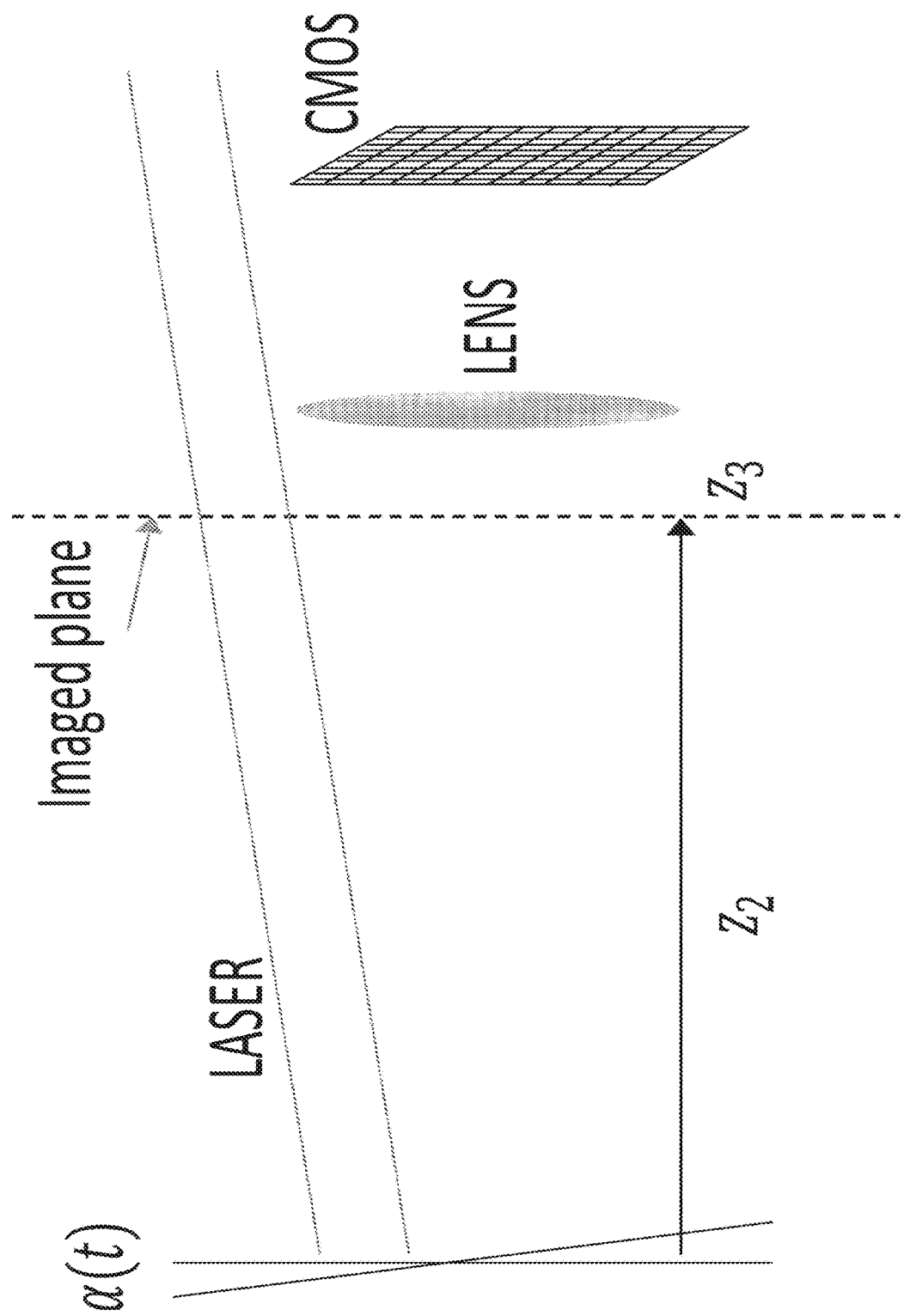
FIG. 7A illustrates an exemplary configuration for capturing a light pattern image(s) and translating an identified spackle pattern for measuring the heartbeat and/or breathing beat of one or more of the occupants, in accordance with some embodiments of the present disclosure.

Reference is now made to FIG. 7A illustrating an exemplary configuration used in accordance with embodiments for capturing a light pattern image(s) and translating an identified spackle pattern for measuring, for example, the heartbeat and/or breathing beat of one or more of the occupants breathing while the vehicle is moving.

Assuming the illuminator is almost parallel to the image sensor optical axis, the translation of the speckle pattern of the CMOS is according to the following Eq:

$$T(t) = 2\frac{z_2}{M}\alpha(t)$$

$$M = \frac{z_3 - F}{F}$$

$$M = \frac{F}{z}$$

Where:

| | |
|---|---|
| $\Phi$ | lens aperture |
| $\lambda$ | wavelength |
| M | magnification |
| $z_2$ | distance from object to imaged plane |
| $z_3$ | distance from imaged plane to lens |
| F | focal length |
| D | laser spot diameter on surface |
| $\alpha(t)$ | surface tilt |
| T(t) | speckle translation on CMOS |
| S | defocused spot size on CMOS |
| $\Delta x$ | CMOS pixel size |
| $f_s$ | camera sampling rate |
| z | distance between CMOS and focal plane |

To measure the speckle size on the captured image, the primary speckle size is reduced by the system magnification:

$$d_{sp} = \frac{\lambda z_2}{DM}$$

The defocused spot size (circle of confusion) is given by the lens aperture ($z_2 \gg z_3$) as follows:

$$S = \Phi\frac{(z_2 + z_3 - z_3)F}{(z_3 - F)(z_2 + z_3)} \approx \frac{\Phi}{M}$$

We find that $$\frac{S}{d_{sp}}$$

does not depend on M:

$$\frac{S}{d_{sp}} = \frac{\Phi D}{\lambda z_2}$$

That may be expressed typical values which are calculated for example as follows:

$$d_{sp} = \left(\frac{\lambda}{830\,\text{nm}}\right)\left(\frac{z_2}{0.5\,\text{nm}}\right)\left(\frac{1\,\text{mm}}{D}\right)\left(\frac{5}{M}\right)\left(\frac{6\mu m}{\Delta x}\right)14\ \text{pixels}$$

$$S = \left(\frac{\Phi}{1\,\text{mm}}\right)\left(\frac{5}{M}\right)\left(\frac{6\mu m}{\Delta x}\right)33\ \text{pixels}$$

$$\frac{S}{d_{sp}} = \left(\frac{\Phi}{1\,\text{mm}}\right)\left(\frac{D}{1\,\text{mm}}\right)\left(\frac{830\,\text{nm}}{\lambda}\right)\left(\frac{0.5\,\text{m}}{z_2}\right)2.4$$

Figure 7B:
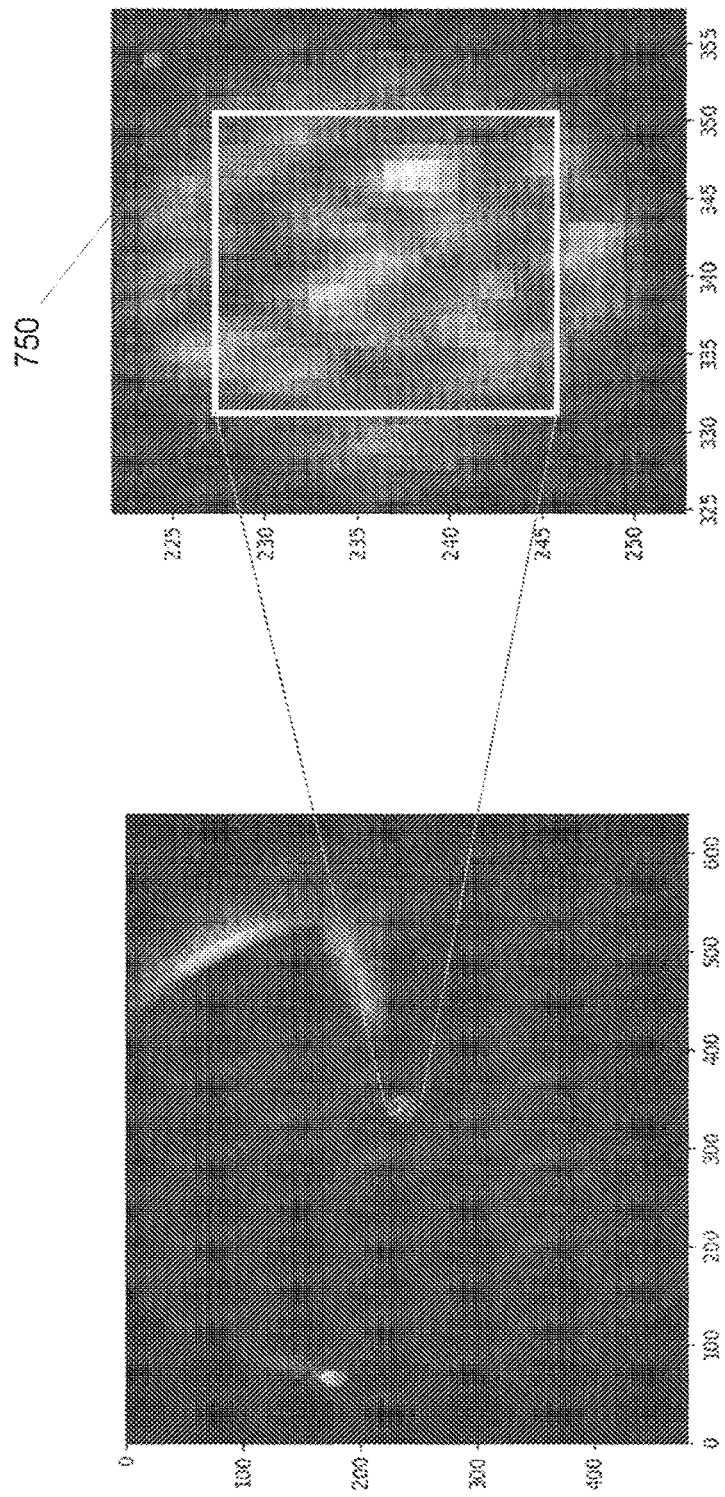
FIG. 7B shows exemplary captured images, in accordance with some embodiments of the present disclosure.
Figure 7C:
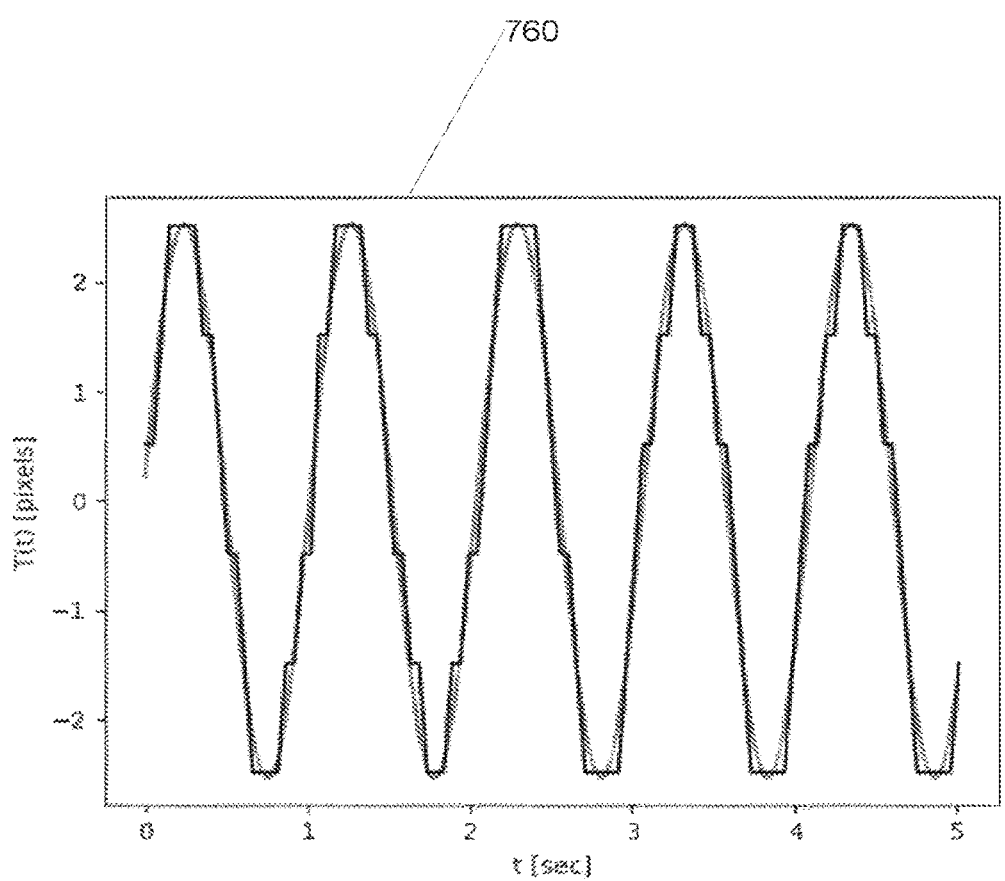
FIG. 7C-7E shows exemplary graph results, suitable for incorporation in accordance with embodiments.
Figure 7D:
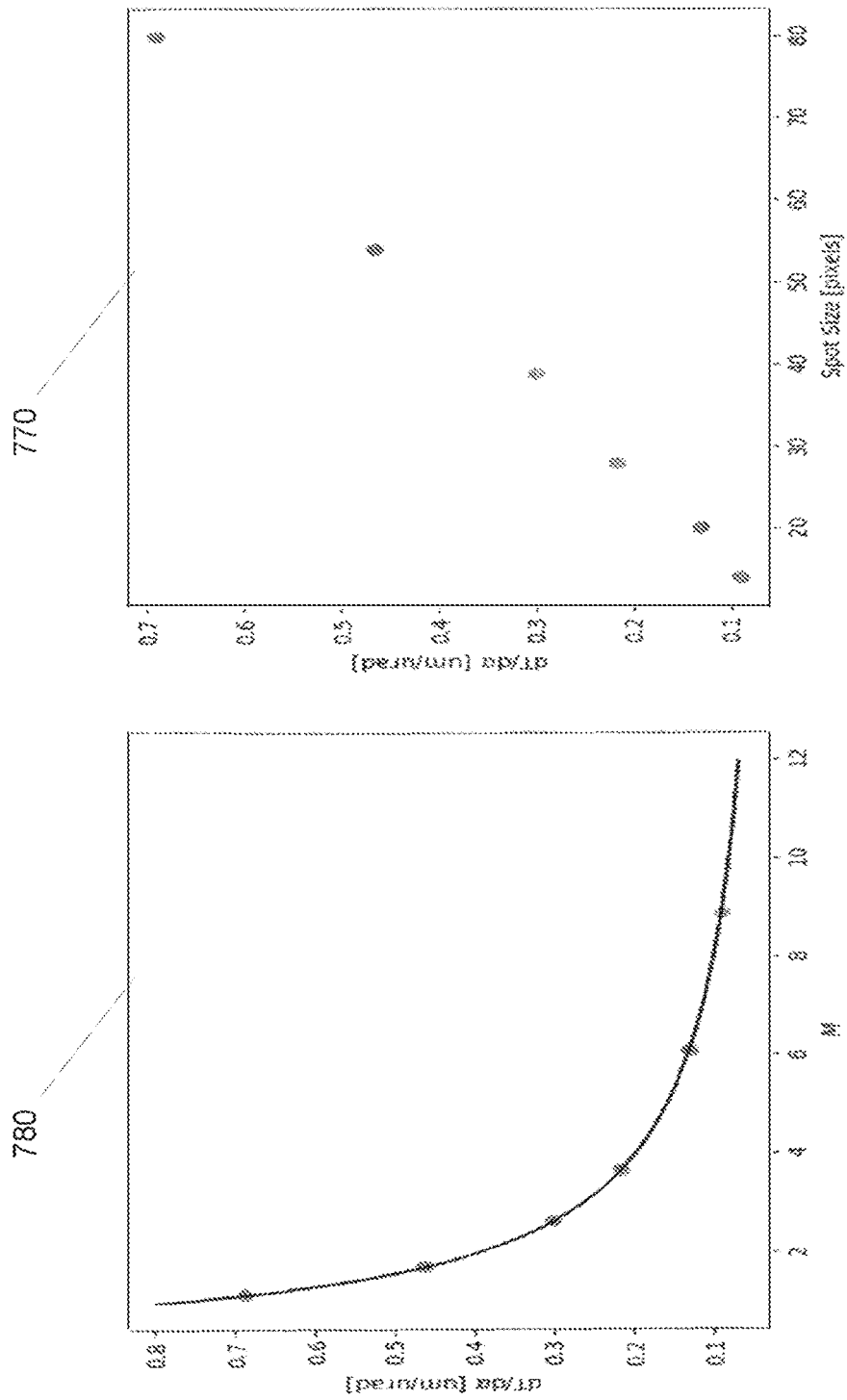
Figure 7E:
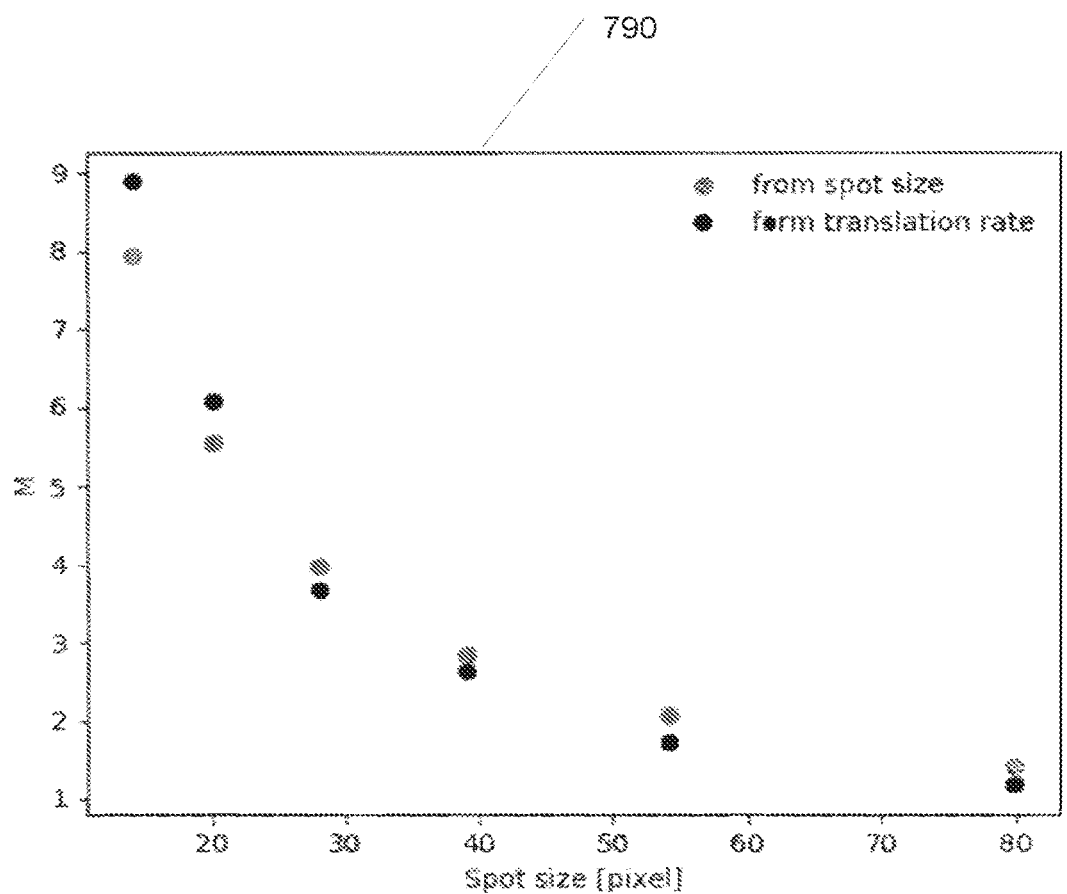

FIG. 7B shows exemplary captured image 750, in accordance with embodiments. In these images, the displacement of each speckle pattern relative to the initial pattern is identified. Thereafter, the speckle translation amplitude in pixels is extracted using, for example, a sine fit such as the sin fit graph 760 of FIG. 7C.

Accordingly, the rate is extracted directly from the translation measurement. The translation rate is linear with spot size as shown in graphs 770 and 780 of FIG. 7D. Additionally, the M of each measurement is calculated from dT/dα and compared with M form the spot size as shown for example in graph 790 of FIG. 7E.

At the next step, the expected measurements limits may be extracted, such as the maximal linear and angular velocities that allow speckle tracking. To avoid boiling the surface linear velocity perpendicular to the beam should be:

$$\frac{v}{f_s} \ll D$$

$$v \ll Df_s$$

In some cases, the translation of the speckle field should be smaller than the size of the spot in the image:

$$2\frac{z_2}{M}\alpha\frac{1}{f_s} < \frac{\Phi}{M}$$

$$\alpha < \frac{\Phi f_s}{2z_2}$$

Accordingly, by using the typical values the following inequalities are calculated $$v \ll \left(\frac{D}{1\,\text{mm}}\right)\left(\frac{f_s}{200\,\text{Hz}}\right)20\,\frac{\text{cm}}{\text{sec}}$$

$$\alpha < \left(\frac{\Phi}{1\,\text{mm}}\right)\left(\frac{f_s}{200\,\text{Hz}}\right)\left(\frac{0.5\,\text{m}}{z_2}\right)11.4\,\frac{\text{deg}}{\text{sec}}$$

Based on these inequalities we expect that at $f_s \sim 200$ Hz the occupant will have to be almost still in order to measure his vital signs.

In accordance with embodiments, the maximal exposure time may be also estimated. Assuming the speckles will blur insignificantly during the exposure time if:

$$\dot{T}\tau < d_{sp}$$

where $\dot{T}$ is the speckle translation speed in pixels/see, and $\tau$ is the exposure time. For typical values we find:

$$\tau < \left(\frac{d_{sp}}{4\,pix}\right)\left(\frac{1\,pix/msec}{\dot{T}}\right)4\ \text{msec}$$

Using $$T = 2\frac{z_2}{M}\alpha$$

we obtain we following values:

$$\tau < \frac{d_{sp}M}{\frac{1}{2}z_2\dot{\alpha}} = \frac{1}{2}\frac{\lambda}{D\dot{\alpha}}\frac{\dot{\alpha}}{-41-} < \frac{1}{2}\frac{\lambda}{D\tau}$$

τ that will allow the maximal $\dot{\alpha}$ for the given $$f_s\left(\dot{\alpha} < \frac{\Phi f_s}{2z_2}\right),$$

e.g. the system will be therefore limited by $f_s$:

$$\tau < \frac{\lambda z_2}{Df_s\Phi} = \left(\frac{\lambda}{830\,\text{nm}}\right)\left(\frac{z_2}{0.6\,\text{m}}\right)\left(\frac{1\,\text{mm}}{D}\right)\left(\frac{200\,\text{Hz}}{f_s}\right)\left(\frac{1\,\text{mm}}{\Phi}\right)2.5\,\text{msec}$$

EXPERIMENTAL DATA

Figure 8A:
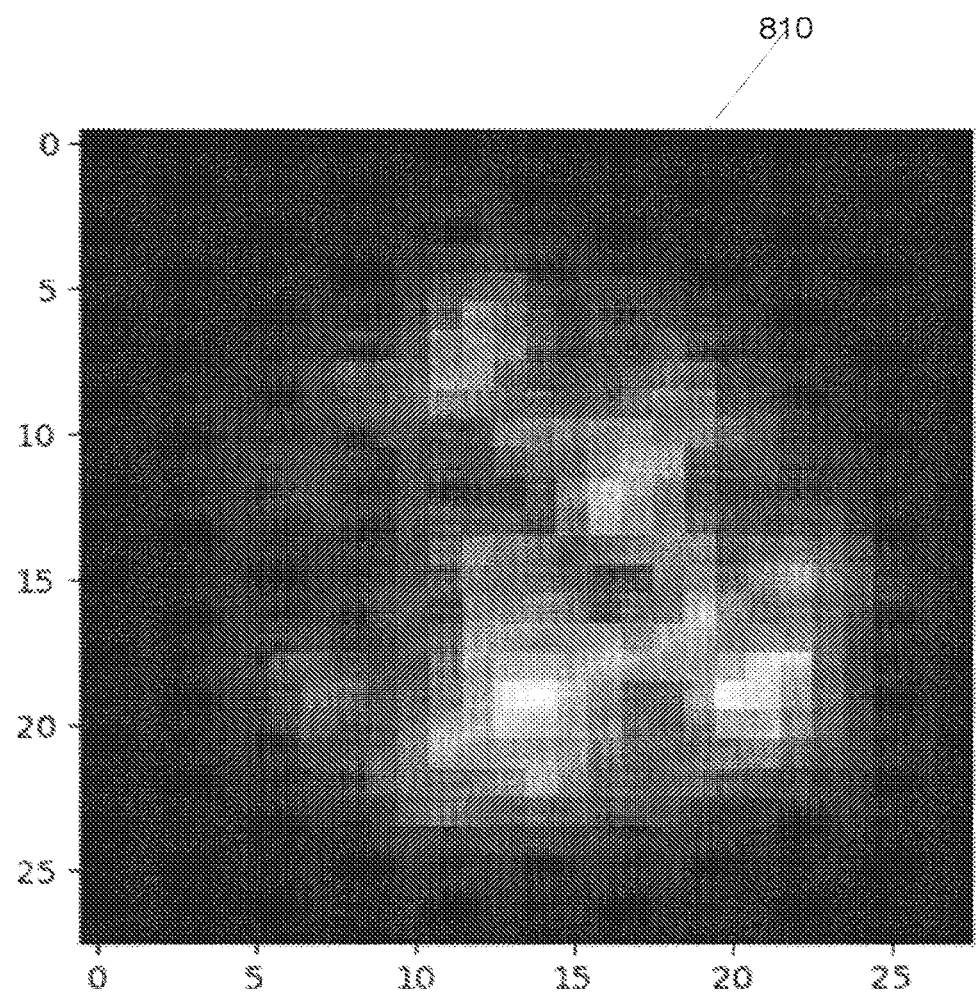
FIG. 8A shows an exemplary magnification of a captured image of an occupant's chest, suitable for incorporation in accordance with embodiments.

FIG. 8A shows an exemplary magnification of a captured image 810 of an occupant chest suitable for incorporation in accordance with embodiments. The image comprises reflected light using an illuminator including a laser power of an 830 nm illuminating the occupant chest area. The captured image 810 shows characteristic features including detected changes to the speckle pattern. As mentioned hereinabove by analyzing the speckle pattern for lateral translation which is indicative of a tilt of the reflecting object with respect to the image sensor the occupant heartbeat may be detected. The tilt which may be very minor, for example, on a scale of micro-radians, may be derived from the translational velocity of one or more speckle pattern point(s) over time (consecutive frames). The lateral speckle pattern translation may be derived from the analysis of the diffused light pattern element(s) depicted in a plurality of consecutively captured images.

Figure 8B:
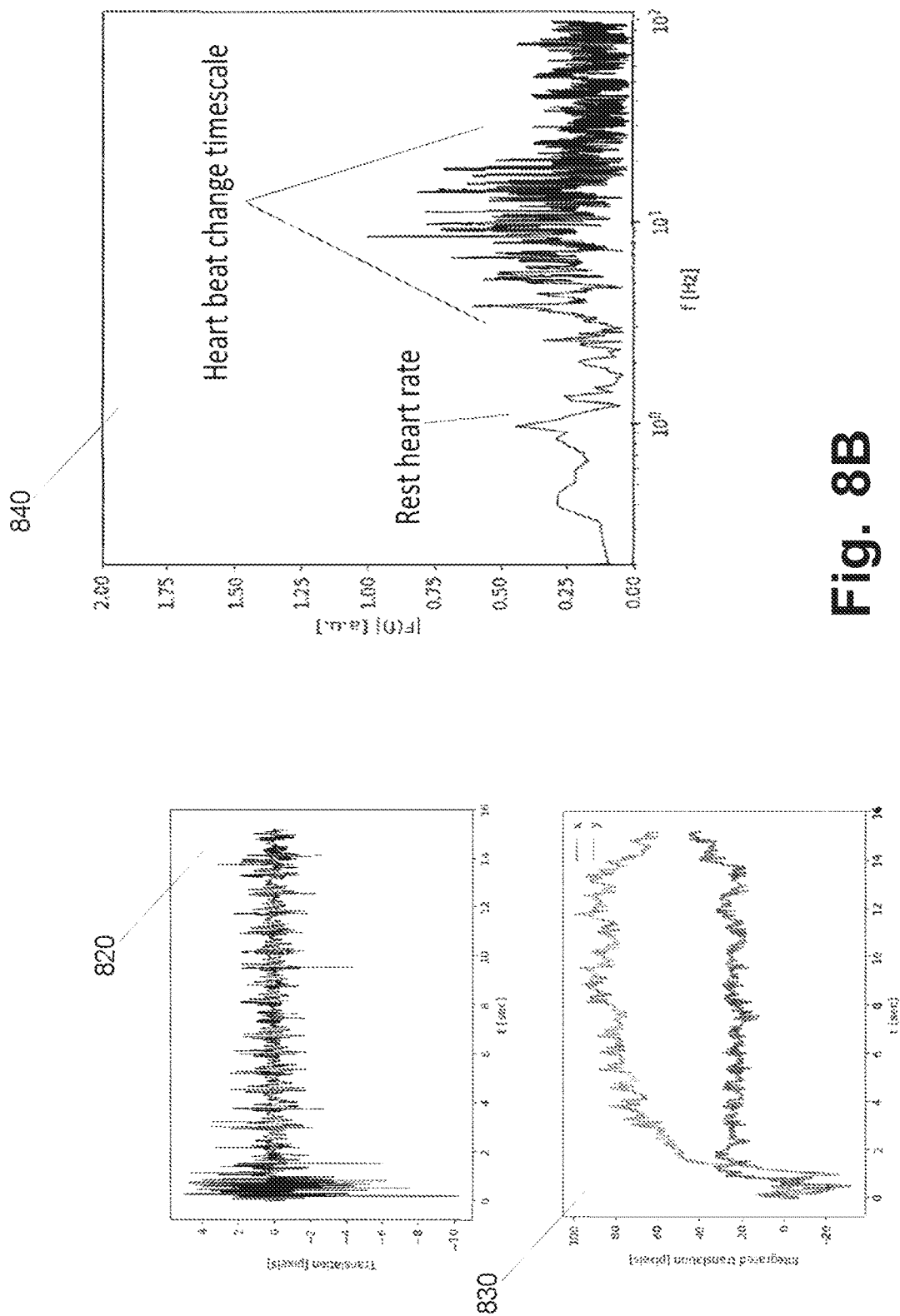
FIG. 8B-8D shows exemplary graph results, suitable for incorporation in accordance with embodiments.

FIG. 8B shows respectively graphs results 820 830 and 840 of processed captured images of an occupant, where the occupant is not breathing and only his heartbeats are detected, in accordance with embodiments. Graph 840 shows exemplary spectrum (fft) of the processed images. In this example the following parameters were used:

$f_s$=200 Hz exposure=5000 μs D=1 mm S=20 pixels (M=29)

Figure 8C:
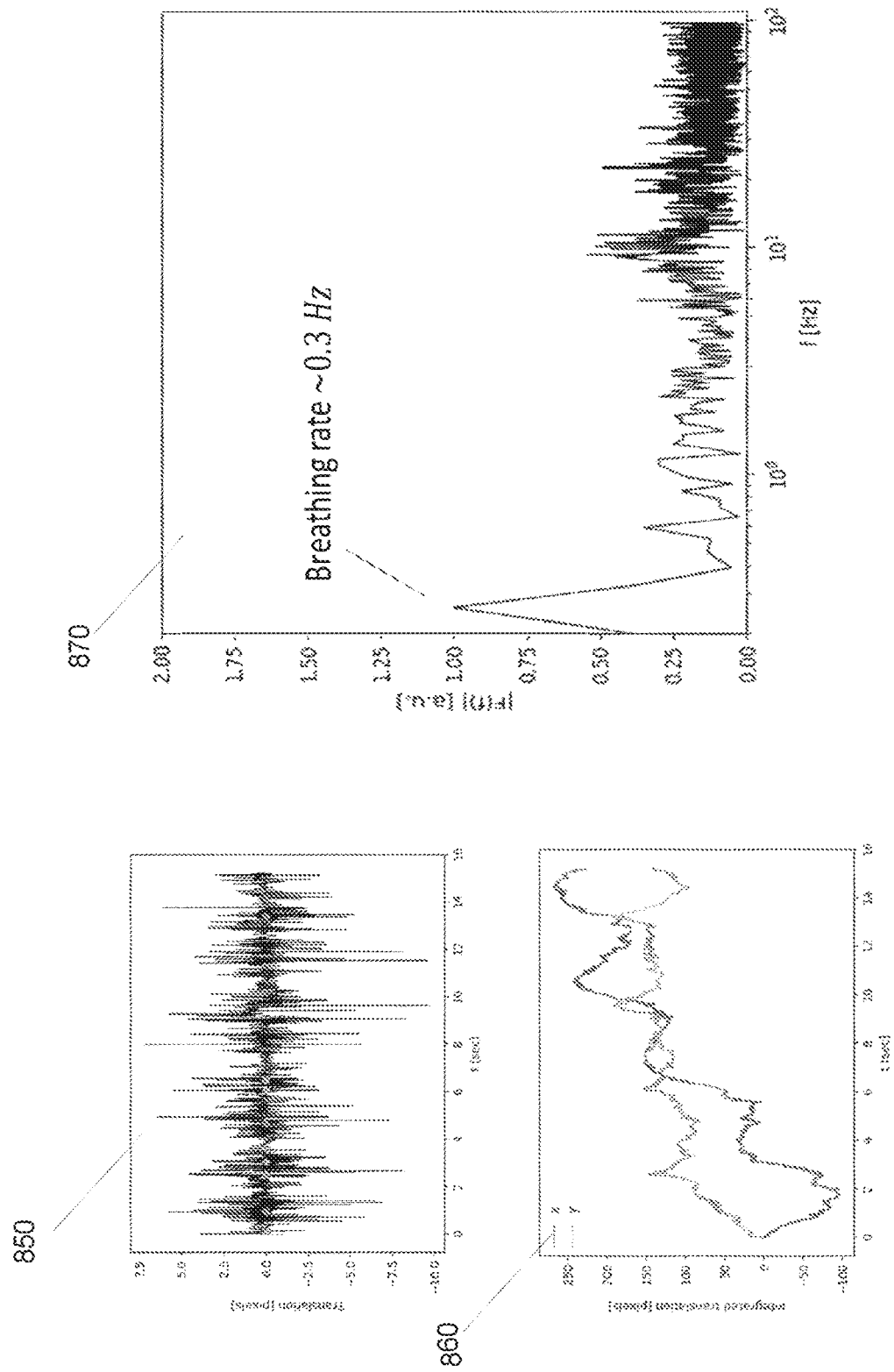

FIG. 8C shows respectively graphs results 850 860 and 870 of processed captured images of an occupant in a vehicle including the occupant heartbeat change while the occupant is breathing normally, in accordance with embodiments. Graph 870 shows exemplary spectrum (fft) of the processed images. Specifically, in scenario the occupants breathing is strong compared to his heartbeat and therefore masks it. In this example, the same parameters of FIG. 8B were used.

Figure 8D:
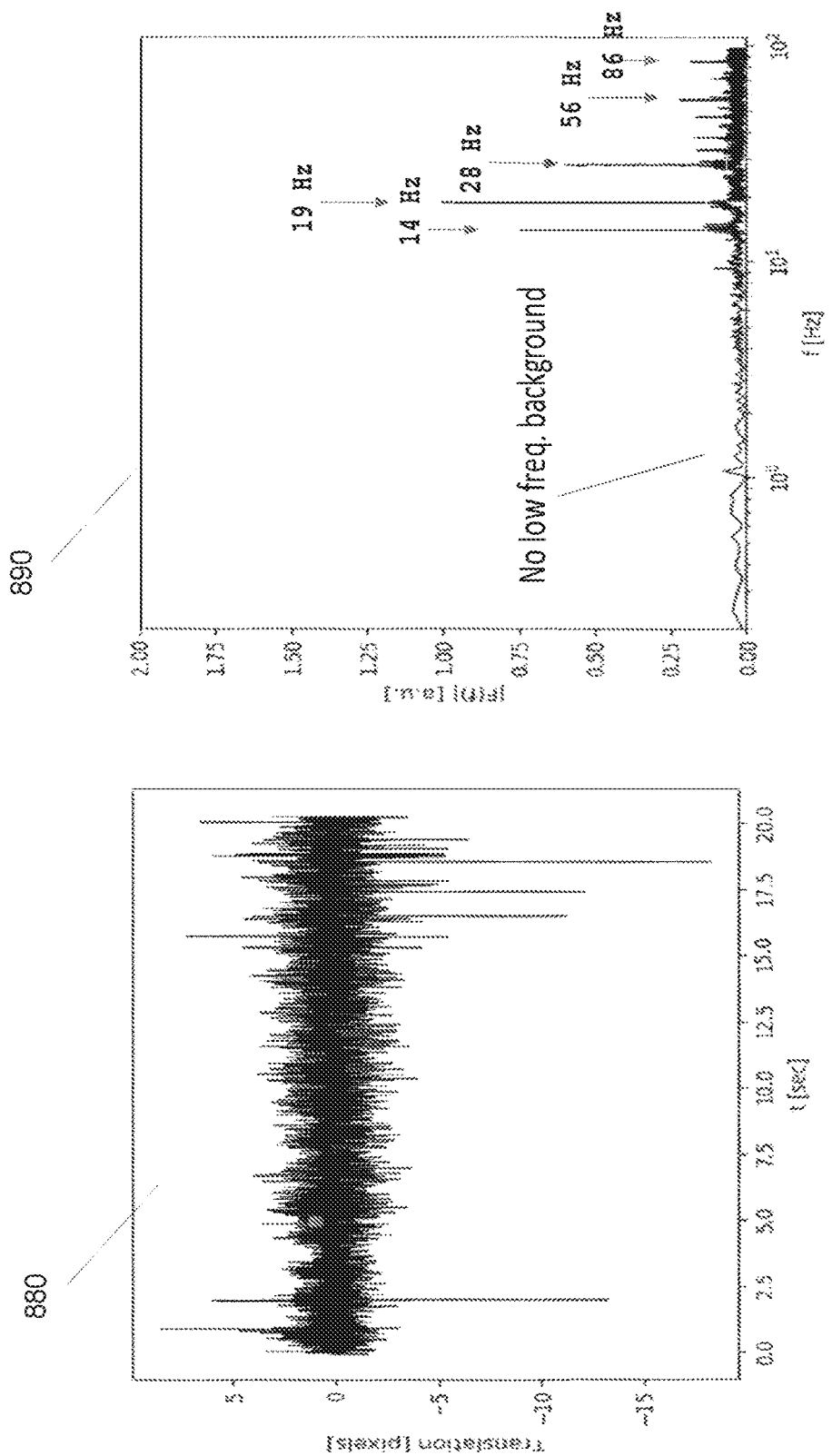

FIG. 8D shows respectively graphs results 880 and 890 of processed captured images of an empty vehicle (without any occupants in a vehicle), hence neither heartbeat or breathing are detected, in accordance with embodiments. In this example the measurements were performed in a FIAT 500 car and the sensing system was positioned on the dashboard and the following parameters were included: $f_s$=200 Hz exposure=5000 μs $z_2$=77 cm to driver's chest.

$z_2$=96 cm to the driver's seat.

D=1 mm, S=20 pixels (M=29)

In some embodiments, the sensing system does not analyze the data collected, and the sensing module relays data to a remote processing and control unit, such as a back end server. Alternatively or in combination, the sensing system may partially analyze the data prior to transmission to the remote processing and control unit. The remote processing and control unit can be a cloud based system which can transmit analyzed data or results to a user. In some embodiments, a handheld device is configured to receive analyzed data and can be associated with the sensing system. The association can be through a physical connection or wireless communication, for example.

In some embodiments, the sensing system comes equipped with memory with a database of data stored therein and a microprocessor with analysis software programmed with instructions. In some embodiments, the sensing system is in communication with a computer memory having a database stored therein and a microprocessor with analysis software programmed in. The memory can be volatile or non-volatile in order to store the measurements in the memory. The database and/or all or part of the analysis software can be stored remotely, and the sensing system can communicate with the remote memory via a network (e.g. a wireless network) by any appropriate method.

In various embodiments of the invention, the conversion of the raw data to medical information may be performed either locally (with a processor and software supplied with the sensing system) or remotely. Heavier calculations for more complicated analyses, for example, can be performed remotely.

In further embodiments, the system disclosed here includes a processing unit which may be a digital processing device including one or more hardware central processing units (CPU) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, by way of non-limiting examples, server computers, desktop computers, laptop computers, notebook computers, sub-notebook computers, netbook computers, notepad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random-access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing-based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

In some embodiments, the system disclosed herein includes one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media. In some embodiments, the system disclosed herein includes at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof. In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

In some embodiments, the system disclosed herein includes software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the system disclosed herein includes one or more databases, or use of the same. In view of the disclosure provided herein, those of skill in the art will recognize that many databases are suitable for storage and retrieval of information as described herein. In various embodiments, suitable databases include, by way of non-limiting examples, relational databases, non-relational databases, object-oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional elements.

It is to be understood that where the claims or specification refer to "a" or "an" element, such reference is not be construed that there is only one of that elements. It is to be understood that where the specification states that a component, feature, structure, or characteristic "may", "might", "can" or "could" be included, that particular component, feature, structure, or characteristic is not required to be included. Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described. Methods of the present invention may be implemented by performing or completing manually, automatically, or a combination thereof, selected steps or tasks.

The descriptions, examples, methods and materials presented in the claims and the specification are not to be construed as limiting but rather as illustrative only. Meanings of technical and scientific terms used herein are to be commonly understood as by one of ordinary skill in the art to which the invention belongs, unless otherwise defined. The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for providing medical information of at least one occupant in a vehicle cabin, the system comprising:
   a sensing module comprising:
      an illuminator comprising one or more illumination sources configured to project light in a predefined light pattern on the vehicle cabin;
      at least one image sensor configured to capture sensory data of the vehicle cabin, wherein said sensory data comprises a sequence of two dimensional (2D) images and three dimensional (3D) images of the vehicle cabin, wherein at least one of the 2D images comprises reflections of said predefined light pattern from the one or more occupants in the cabin; and
   a control module comprising at least one processor, said processor is configured to:
      receive said sensory data from said image sensor;
      detect an imminent crash of the vehicle, wherein said sensory data is captured prior to said detection of imminent crash, during said crash and following said crash; and
      analyze said sensory data including the sequence of 2D images and 3D images using one or more analysis methods to provide the medical information of said at least one occupant; and
      assess a medical status of said at least one vehicle occupant following the crash based on said analyzed sensory data.

2. The system of claim 1, wherein said light source comprises one or more optical elements for splitting a single light beam generated by said light source, said one or more optical elements are selected from the group consisting of: diffractive optical element (DOE); split mirrors; and diffuser.

3. The system of claim 1, wherein said sensing module comprises a depth sensor.

4. The system of claim 3, wherein said depth sensor is configured to capture depth data by projecting a light pattern onto the vehicle cabin and wherein the at least one processor is configured to analyze the location of known light pattern elements in said depth data.

5. The system of claim 4 wherein the pose of said at least one occupant is estimated by analyzing the depth data using said computer vision methods.

6. The system of claim 1, wherein the sensing module comprises a micro-vibration sensor.

7. The system of claim 6, wherein the micro-vibration sensor is configured to:
   project light onto the vehicle cabin scene;
   capture a plurality of images, wherein each image of said plurality of images comprises reflected diffused light elements; and
   wherein the processor is configured to:
      receive the captured images; and
      analyze one or more temporal changes in the speckle pattern of at least one of the plurality of reflected diffused light elements in at least some consecutive images of the plurality of images to yield micro-vibration data.

8. The system of claim 1, wherein the sensing module comprises a combination of the image sensor and at least one sensor selected from a group consisting of:
   a depth sensor and a micro-vibration sensor.

9. The system of claim 1, wherein the at least one processor is further configured to classify the at least one vehicle occupant using said computer vision methods by visually analyzing at least one 2D or 3D image of the sequence of images captured by the at least one image sensor.

10. The system of claim 1, wherein the detection of an imminent crash is performed by one or more of:
    vehicle impact sensor; hectic movement detection sensor; and external sensory system.

11. A system for estimating the medical state of one or more occupants in a vehicle cabin following an accident of the vehicle, the system comprising;
    a sensing module comprising:
       an illuminator comprising one or more illumination sources configured to project light in a predefined light pattern on the vehicle cabin;
       at least one image sensor configured to capture sensory data prior to, during and following a crash of said vehicle, said sensory data comprising a sequence of two dimensional (2D) images and three dimensional (3D) images of the vehicle cabin wherein at least one of the 2D images comprise reflections of said predefined light pattern from the one or more occupants in the cabin;
    a control module comprising:
       a memory module; and
       at least one processor, said at least one processor is configured to:
          receive said captured sensory data from the sensing module;
          receive an impact detection signal of an imminent crash of the vehicle;
          store the received sensory data, captured prior to receiving said impact detection signal, in said memory module;
          analyze said received sensory data including the sequence of 2D images and 3D images using computer vision or machine learning algorithm to yield pre-crash assessment data comprising an identification of the one or more occupant's state prior to the crash;
          receive sensory data captured during said crash from the sensing module;
          analyze the received sensory data including the sequence of 2D images and 3D images captured during said crash to yield during-crash assessment data comprising body trajectories of the one or more occupants; and
          provide medical information of said one or more occupants following the crash based on said during-crash assessment data and pre-crash assessment data.

12. The system of claim 11 wherein said at least one processor is further configured to:
    receive sensory data captured following the crash; and
    analyze the received sensory data captured following the crash data using computer vision or machine learning algorithm to yield one or more of post-crash assessment data of said one or more occupants.

13. The system of claim 12 wherein said post-crash assessment data comprises one or more of: heartbeat; respiration rate; body pose; body motion; visible wounds.

14. The system of claim 12 wherein said processor is further configured to combine said post-crash assessment data with said during crash assessment data and said pre-crash assessment data to yield said medical information of said one or more occupants following the crash.

15. The system of claim 13 wherein the heartbeat or respiration rate are identified by:
   analyzing one or more changes in one or more speckle patterns of at least one of the reflections of said predefined light pattern in at least some consecutive images of the plurality of images; and
   identifying the vibrations of the one or more occupants based on said speckle pattern analysis.

16. The system of claim 11, wherein said one or more of the body pose, body motion, and visible wounds are detected by analyzing the sequence of 2D images or 3D images of the vehicle cabin.

* * * * *